United States Patent [19]

Yabe et al.

[11] Patent Number: 4,888,639

[45] Date of Patent: Dec. 19, 1989

[54] ENDOSCOPE APPARATUS HAVING INTEGRATED DISCONNECTABLE LIGHT TRANSMITTING AND IMAGE SIGNAL TRANSMITTING CORD

[75] Inventors: Hisao Yabe; Koji Takamura, both of Hachioji, Japan

[73] Assignee: Olympous Optical Co., Ltd., Tokyo, Japan

[21] Appl. No.: 197,074

[22] Filed: May 20, 1988

[30] Foreign Application Priority Data

May 22, 1987 [JP] Japan .................. 62-125154
Sep. 9, 1987 [JP] Japan .................. 62-227209
Feb. 2, 1988 [JP] Japan .................. 63-22268

[51] Int. Cl.$^4$ .................. A61B 1/04; H04N 7/18
[52] U.S. Cl. .................. 358/98; 128/6
[58] Field of Search .................. 358/98, 210; 128/6

[56] References Cited

U.S. PATENT DOCUMENTS 4,539,586 9/1985 Danna et al. .
4,755,873 7/1988 Kobayashi .................. 358/98

FOREIGN PATENT DOCUMENTS 52-58488 5/1977 Japan .
54-97322 8/1979 Japan .
60-80429 5/1985 Japan .

Primary Examiner—Howard W. Britton
Assistant Examiner—Victor R. Kostak
Attorney, Agent, or Firm—Armstrong, Nikaido, Marmelstein, Kubovcik & Murray

[57] ABSTRACT

The endoscope apparatus is provided with an endoscope, a light source apparatus and an imaging controlling apparatus. The endoscope comprises an elongate insertable part having an observing window and illuminating window in the tip part, an image forming optical system opposed to the observing window within the tip part of the insertable part, an illuminating light transmitting system inserted through the insertable part and emitting an illuminating light out of the illuminating window, an imaging apparatus imaging an object image formed by the image forming optical system and a first signal transmitting system connected to the imaging apparatus. The entrance end side of the illuminating light transmitting system and the base end side of the first signal transmitting system are integrated and are provided at the end with a connecting part. A second signal transmitting system connected to the first signal transmitting system is extended from the imaging controlling apparatus. A first connecting apparatus removably connects the entrance end of the illuminating light transmitting system in the connecting part to the light source apparatus and a second connecting apparatus removably connects the base end of the first signal transmitting system and the end of the second signal transmitting system in the connecting part with each other. The first signal transmitting system relating at least to imaging signals are preferably made substantially equal in the characteristic impedance.

28 Claims, 17 Drawing Sheets

ENDOSCOPE APPARATUS HAVING INTEGRATED DISCONNECTABLE LIGHT TRANSMITTING AND IMAGE SIGNAL TRANSMITTING CORD

BACKGROUND OF THE INVENTION

1. Field of the Invention

This invention relates to an endoscope apparatus provided with an endoscope having an imaging means and illuminating light transmitting means, a light source apparatus and an imaging controlling apparatus.

2. Related Art Statement

Recently, there is extensively used an endoscope whereby, by inserting an elongate insertable part into a body cavity, organs within the body cavity can be observed and, as required, various curing treatments can be made.

Also, an electronic endoscope wherein such solid state imaging device as a charge coupled device (CCD) is used for the imaging means is practiced. The recent progress of the semiconductor technique is so remarkable that superior solid state imaging devices are being continuously developed.

An electronic endoscope apparatus is formed of an endoscope body (electronic endoscope) provided with the above mentioned solid state imaging device, an imaging controlling apparatus driving the above mentioned solid state imaging device and processing an image signal from this solid state imaging device to output it as a video signal and a light source apparatus feeding an illuminating light to the above mentioned endoscope body.

There are various modes of connecting the above mentioned endoscope body, light source apparatus and imaging controlling apparatus with one another.

For example, in the gazette of Japanese patent application laid open No. 80429/1985 (with priorities claimed on U.S. patent application Ser. No. 539,982 and U.S. Pat. No. 4,538,586), there is disclosed an endoscope apparatus wherein an imaging controlling apparatus and a light source apparatus are integrated with each other and an endoscope body is connected to this integrated apparatus by using a connector integrating an electrically connecting electric connector with an illuminating light connecting light connector. However, when the solid state imaging device is new as described above, the imaging controlling apparatus controlling it must be also new. In such case, there is a problem that, if the image controlling apparatus is integral with the light source apparatus, the unchanged light source apparatus will be also replaced and will therefore become useless, also, if the electric connector and light connector are integral with each other, both connectors will be simultaneously fitted and removed, a high assembling precision will be required and the fitting and removing will be a problem. Further, there is a problem that, if the imaging controlling apparatus and light source apparatus are integral with each other, as an imaging signal cable passes through the light source apparatus, the signals will be likely to be influenced by noises and the like.

Therefore, if the imaging controlling apparatus and light source apparatus are made separate from each other, even in the case of replacing the imaging controlling apparatus, the light source apparatus will be able to be continued to be used as it is, it will be economical and the above described problems will be solved.

In case the imaging controlling apparatus and light source apparatus are thus made separate from each other, the endoscope body and imaging controlling apparatus will have to be electrically connected with each other and the illuminating light will have to be connected between the endoscope body and light source apparatus. Such mode of connecting them as is shown, for example, in FIGS. 31 or 32 is considered.

In the example shown in FIG. 31, an endoscope body 1 is provided with an elongate insertable part 2 and a thick operating part 3 connected to the rear end of this insertable parts 2. A universal cord 4 is extended out of the above mentioned operating part 3 and is branched into a light guide cord 5 and imaging signal cord 6. The light guide cord 5 is provided at the tip with a light guide plug 7 and the imaging signal cord 6 is provided at the tip with an imaging signal plug 8.

On the other hand, a separate light source apparatus 11 and imaging controlling apparatus 12 are provided respectively with a light guide socket 13 and imaging signal socket 14. The light guide plug 7 is to be connected to the above mentioned light guide socket 13. The imaging signal plug 8 is to be connected to the above mentioned imaging signal socket 13.

In the example shown in FIG. 32, the universal cord 4 is provided at the tip with the light guide plug 7 from which the imaging signal cord 6 is extended and is provided at the tip with the imaging signal plug 8.

However, the example shown in FIG. 31 or 32 has problems that, when the light guide plug 7 is to be connected to the light guide socket 13, the imaging signal cord 6 will swing, when the endoscope body 1 is to be washed or carried, the light guide cable 5 and imaging signal cable 6 will swing and the light guide plug 7 and imaging signal plug 8 will collide with each other to be likely to be broken and thus the handlability is poor.

In the example shown in FIG. 31, when the endoscope body 1 is connected to the light source apparatus 11 and imaging controlling apparatus 12 to make an inspection, either of the light guide cord 5 and imaging signal cord 6 will be protruded or entangled to obstruct the inspection.

OBJECT AND SUMMARY OF THE INVENTION

An object of the present invention is to provide an endoscope apparatus whereby a light source apparatus and imaging controlling apparatus can be made separate from each other and the operatability of the endoscope can be improved.

Another object of the present invention is to provide an endoscope apparatus whereby a light source apparatus and imaging controlling apparatus can be made separate from each other, the operatability of the endoscope can be improved and the deterioration of signals can be prevented.

The endoscope apparatus of the present invention is provided with an endoscope, a light source apparatus and an imaging controlling apparatus. The above mentioned endoscope is provided with an elongate insertable part having an observing window and illuminating window in the tip part, an image forming optical system provided at the above mentioned observing window within the insertable part and forming an object image, an illuminating light transmitting means inserted through the above mentioned insertable part, opposed at the exit end to the above mentioned illuminating window and emitting an illuminating light through this illuminating window, an imaging means for imaging the object image formed by the above mentioned imaging optical system and a first signal transmitting means connected to the above mentioned imaging means. The above mentioned illuminating light transmitting means on the entrance end and the above mentioned first signal transmitting means on the base end are made integral and a connecting part is provided at the end. The above mentioned light source apparatus feeds an illuminating light to the above mentioned illuminating light transmitting means. The above mentioned imaging controlling apparatus controls the above mentioned imaging means. A second signal transmitting means to be connected to the above mentioned first signal transmitting means is extended from this imaging controlling apparatus. There are provided a first connecting means removably connecting the above mentioned light source apparatus with the entrance end of the illuminating light transmitting means in the above mentioned connecting part and a second connecting means removably connecting the end of the above mentioned second signal transmitting means with the base end of the first signal transmitting means in the above mentioned connecting part. Those connecting means relating at least to imaging signals of the above mentioned first signal transmitting means and second signal transmitting means are preferably substantially equal in the characteristic impedance.

The other features and advantages of the present invention will become apparent enough with the following explanation.

BRIEF DESCRIPTION OF THE DRAWINGS

FIG. 1 is a perspective view of an endoscope apparatus.

FIG. 2 is a side view showing a connecting part as magnified.

FIG. 3 is an explanatory view showing the formation of the endoscope apparatus.

FIGS. 4 to 10 relate to the first example of a solid state imaging device.

FIG. 4 is a plan view of the solid state imaging device.

FIG. 5 is a sectioned view of the solid state imaging device.

FIG. 6 is a bottom view of the solid state imaging device.

FIG. 7 is a sectioned view showing a substrate molding mold.

FIG. 9 is an explanatory view showing a bonding step.

FIG. 10 is a sectioned view of an endoscope tip part incorporating a solid state imaging device.

FIG. 11(A) is a plan view of the solid state imaging device.

FIG. 12(A) is a plan view of the solid state imaging device.

FIGS. 13 and 14 relate to the fourth example of a solid state imaging device.

FIG. 14 is a sectioned view showing a substrate molding mold.

FIGS. 16 and 17 show example of a related art.

FIG. 17 is a sectioned view showing a substrate molding mold.

FIG. 20 is an explanatory view showing the formation of an endoscope apparatus.

FIG. 21 is an explanatory view showing a light source apparatus and imaging controlling apparatus in this embodiment as connected with a fiber scope and externally fitted television camera.

FIG. 22 is an elevation showing a connecting part of an endoscope body with a light source apparatus and imaging controlling apparatus.

FIG. 23 is a plan view of the apparatus of FIG. 22.

FIG. 24 is a right side view of the apparatus of FIG. 22;

FIG. 25 is a perspective view of an endoscope apparatus.

FIG. 26 is a side view showing a connecting part as magnified.

FIG. 27 is an explanatory view showing a locking mechanism of a light guide plug.

FIG. 29 is an explanatory view showing the formation of an endoscope apparatus.

FIG. 30 is a circuit diagram showing an example of a connection sensing means.

FIG. 31 is an explanatory view showing an example of the connection of a separate imaging controlling apparatus and light source apparatus with an endoscope body.

FIG. 32 is an explanatory view showing another example of the connection of a separate imaging controlling apparatus and light source apparatus with an endoscope body.

DETAILED DESCRIPTION OF PREFERRED EMBODIMENTS

Figure 1:
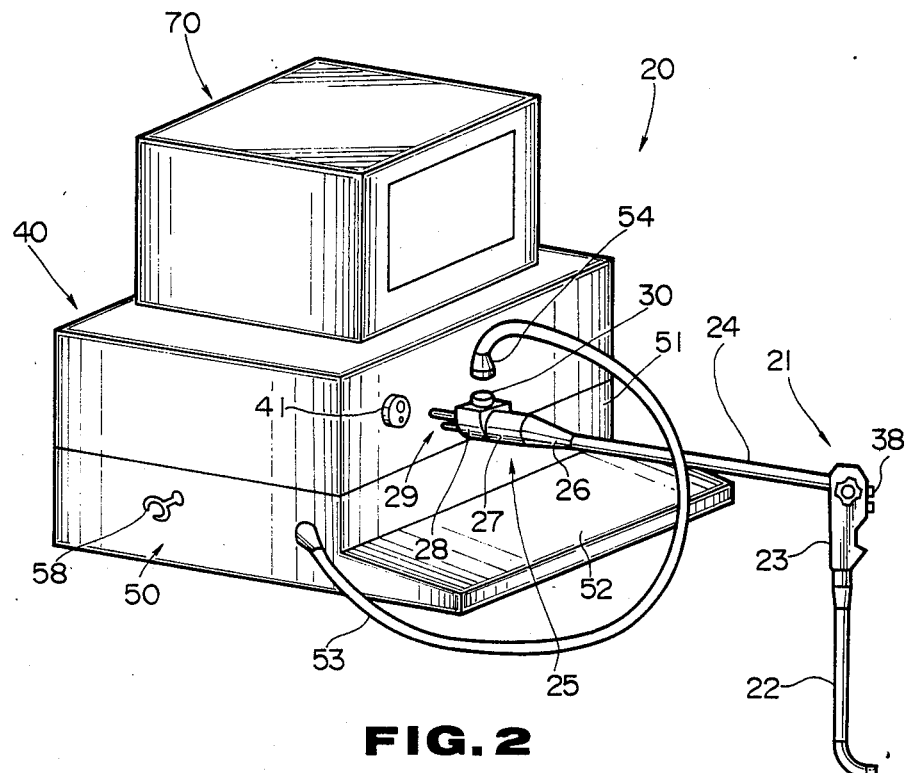
FIGS. 1 to 3 relate to the first embodiment of the present invention.
Figure 2:
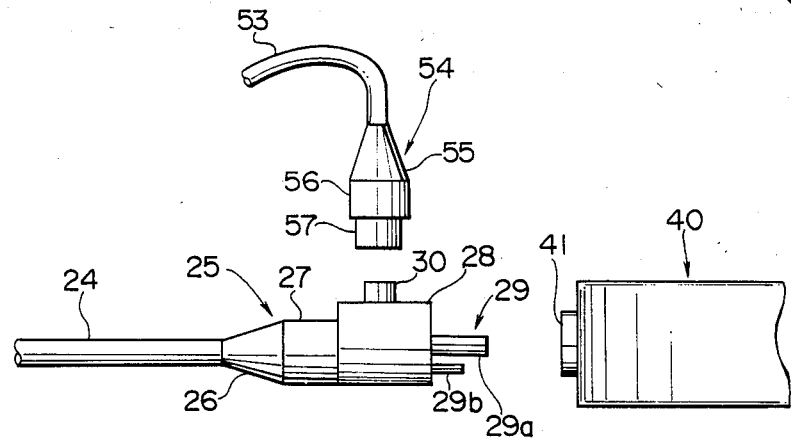
Figure 3:
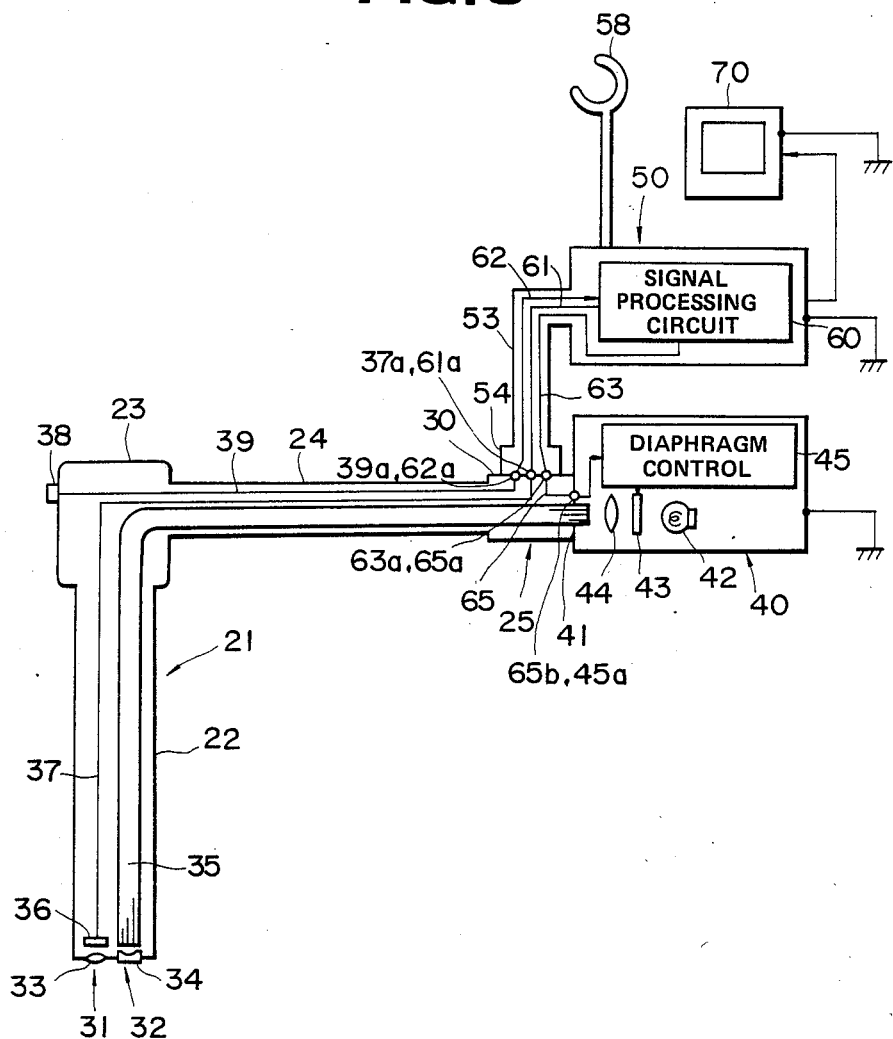
Figure 4:
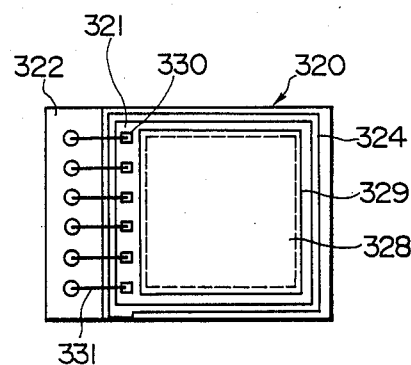
Figure 5:
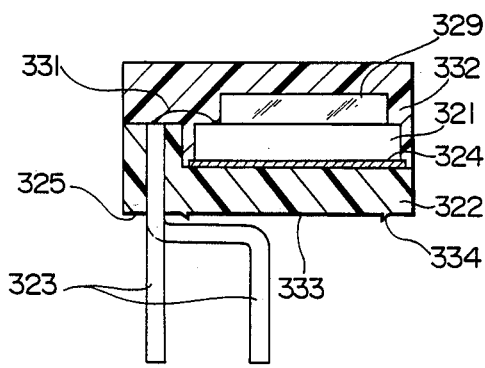
Figure 6:
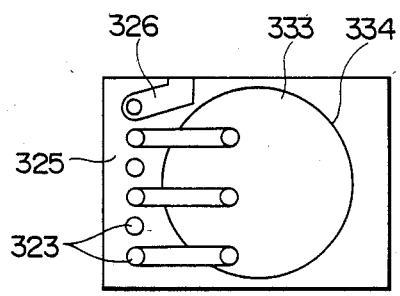

FIGS. 1 to 3 show the first embodiment of the present invention.

As shown in FIG. 1 an endoscope apparatus 20 is formed of an endoscope body 21, a light source apparatus 40 and imaging controlling apparatus 50 connected with this endoscope body 21 and an observing monitor 70 connected with the above mentioned imaging controlling apparatus 50.

The above mentioned endoscope body 21 is provided with an elongate, for example, flexible insertable part 22 to the rear end of which an operating part 23 is connected. A universal cord 24 as an integrating means is extended sidewise from the above mentioned operating part and is provided at the tip with a light guide plug 25 as a connecting part. The above mentioned operating part 23 is provided with an operating part switch 38 for making such control of the above mentioned imaging controlling apparatus 50 as freezing image frames.

As shown in FIG. 2, the above mentioned light guide plug 25 is provided with a buckling preventing part 26 tapered to be expanded in diameter on the tip side, a thick gripping part 27 and a plug body 28 connected in turn to the tip of the above mentioned universal cord 24. The above mentioned plug body 28 is provided at the tip with a light guide connecting part 29. By the way, this light guide connecting part 29 is provided with not only a light guide connector 29a but also an air and water feeding connector 29b. The above mentioned plug body 28 is provided on the side with an imaging signal socket 30.

On the other hand, the above mentioned light source apparatus 40 is provided, for example, on the left side of the front surface of a housing with a light guide socket 41 removably connectable with the light guide connecting part 29 of the above mentioned light guide plug 25.

The above mentioned imaging controlling apparatus 50 has a panel 51 on the front surface of the housing and is provided with a keyboard 52 on the lower side of this panel 51. An imagine signal cord 53 is extended from the front side of the left side surface of the housing of the above mentioned imaging controlling apparatus 50 and is provided at the tip with an imaging signal plug 54 removably connectable to the above mentioned imaging signal socket 30 provided on the above mentioned light guide plug 25. As shown in FIG. 2, this imaging signal plug 4 is provided with a buckling preventing part 55 tapered to expand in the diameter on the tip end, a thick gripping part 56 and an imaging signal connecting part 57 connected in turn to the tip of the above mentioned imaging signal cord 53. An imaging signal plug hanger 58 which can hang and hold the above mentioned imaging signal plug 54 or imaging signal cord 53 is provided on the left side surface of the housing of the above mentioned imaging controlling apparatus 50.

The interiors of the above mentioned endoscope body 32, light source apparatus 40 and imaging controlling apparatus 50 are formed as shown in FIG. 3.

The above mentioned endoscope body 21 is provided in the tip part of the insertable part 22 with an observing window 31 and illuminating window 32 in which respectively an objective lens optical system 33 and light distributing lens 34 are arranged. A light guide 35 formed, for example, of a fiber bundle as an illuminating light transmitting means is provided on the rear end of the above mentioned light distributing lens 34, is inserted through the above mentioned insertable part 22 and universal cord 24, is extended to the above mentioned light guide plug 25 and is connected at the entrance end to the light guide connector 29a of the light guide connecting part 29.

A solid state imaging device 36 is arranged in the image forming position of the above mentioned objective lens optical system 33. By the way, in the case of using a simultaneous system for the color imaging system, a color filter array in which color filters transmitting respectively the respective color lights of red, green and blue or the like are arranged like a mosaic is provided on the front surface of the above mentioned solid state imaging device 36. An imaging signal cable 37 as a first signal transmitting means is connected to the above mentioned solid state imaging device 36, is inserted through the above mentioned insertable part 22 and universal cord 24, is extended to the above mentioned light guide plug 25 and is connected at the base end to an electric contact 37a of the above mentioned imaging signal socket 30.

In case the solid state imaging device 36 is a four-phase drive interline CCD, the above mentioned electric contact 37a will be generally of about 20 pins.

A switch cable 39 is connected to the above mentioned operating part switch 38, is inserted through the above mentioned universal cord 24 and is connected to an electric contact 39a of the imaging signal socket 30 provided in the above mentioned light guide plug 25. By the way, in case the switch 38 is a single switch, two electric contacts 39a will be required.

On the other hand, the above mentioned light source apparatus 40 is provided with a lamp 42 emitting an illuminating light and has a variable diaphragm 43 controlled by a diaphragm controlling circuit 45 and a condenser lens 44 arranged in turn forward of this lamp 42. When the light guide plug 25 of the endoscope body 21 is connected to the above mentioned light guide socket 41, if the above mentioned lamp 42 is made to emit a light, the illuminating light emitted from this lamp 42 will be adjusted in the light amount by the above mentioned variable diaphragm 43, will then be condensed by the condenser lens and will enter the entrance end of the light guide 35 connected to the light guide connecting part 29 of the above mentioned light guide plug 25.

The above mentioned imaging controlling apparatus 50 is provided with a signal processing circuit 60 driving the solid state imaging device 36 of the endoscope body 21 and processing the output signal of this solid state imaging device 36 so as to be a video signal. An imaging signal cable 61, switch cable 62 and light adjusting signal cable 63 connected each at one end to the above mentioned signal processing circuit 60 and at the other end to the respective electric contacts 61a, 62a and 63a of the above mentioned imaging signal plug 54 are inserted through an imaging signal cord 53 extended from the above mentioned imaging controlling apparatus 50. In case an imaging signal plug 54 is connected to the imaging signal socket 30, the above mentioned imaging signal cable 61 will be connected to the imaging signal cable 37 of the endoscope body 21 through the electric contacts 37a and 61a and the above mentioned switch cable 63 will be connected to the switch cable 39 of the endoscope body 21 through the electric contacts 39a and 63a.

In this embodiment, electric contacts 65a and 65b corresponding respectively to the above mentioned imaging signal socket 30 and light guide connecting part 29 are provided and are connected with each other through a light adjusting signal cable 65 provided within the light guide plug 25. The electric contact 65a on the above mentioned imaging signal socket 30 side is connected to the electric contact 63a of the imaging signal plug 54 connected to the light adjusting signal cable 63 within the above mentioned imaging signal cord 53. The electric contact 65b on the above mentioned light guide connecting part 29 side is connected to the electric contact 45a connected to the diaphragm controlling circuit 45 within the light source apparatus 40. The light adjusting signal from the signal processing circuit 60 within the above mentioned image controlling apparatus 50 will be input into the diaphragm controlling circuit 45 within the light source apparatus 40 through the above mentioned light adjusting signal cables 63 and 65 so that the diaphragm 43 may be controlled so as to, for example, automatically adjust the light with this light adjusting signal. The above mentioned electric contacts 65a and 65b are respectively two contacts.

Now, in such formation, when the signal cable within the universal cord 24 and the signal cable within the imaging signal cord 53 extended from the imaging controlling apparatus 50 are signal cables of different kinds, that is, both signal cables are different, in characteristic impedance, the signal will be reflected at the connecting part of both signal cables and such disadvantage as deterioration of the picture quality will be produced. If both signal cables are of different characteristic impedance, the waveform will be deformed, the picture quality will deteriorate, undesireable radiation will be produced and the peripheral electronic devices will be adversely influenced.

Therefore, in this embodiment, the signal cables relating at least to imaging signals among the signal cables within the above mentioned endoscope body 21 and imaging signal cord 53, that is, the imaging signal cables 37 and 61 transmitting driving signals and video signals between the solid state imaging device 36 and signal processing circuit 60 are signal cables of the same kind having equal characteristic impedance. By the way, the signal cables having equal characteristic impedance may be cables exactly same in structure, conductor material and thickness or cables different in the structure but equal in characteristic impedance. By the way, even in case the length of the insertable part 22 of the endoscope body 21 is different and therefore the length of the imaging signal cable 37 is different, the signal cables of the same kind will be used. The characteristic impedance of the electric contacts 37a and 61a connecting the above mentioned imaging signal cables 37 and 61 is made equal to the characteristic impedance of the above mentioned signal cables 37 and 61.

The video signal produced by the signal processing circuit 60 within the above mentioned imaging controlling apparatus 50 will be input into the observing monitor 70.

The sheaths of the above mentioned light source apparatus 40, imaging controlling apparatus 50 and monitor 70 are made, for example, of a metal, have substantially a conductivity and are earthed. That is to say, the sheaths of the light source apparatus 40, imaging controlling apparatus 50 and monitor 70 form shielding means. The signal processing circuit 60 is insulated from the image controlling apparatus 40. The diaphragm controlling circuit 45 is insulated from the light source apparatus 40. Also, the endoscope body 21 and imaging signal cord 53 are insulated from the sheaths of the imaging controlling apparatus 50 and light source apparatus 40. By the way, one of the light source apparatus 40 and imaging controlling apparatus 50 may be shielded.

The operation of this embodiment formed as described above shall be explained in the following.

The endoscope body 21 is connected with the light source apparatus 40 and imaging controlling apparatus 50. That is to say, the light guide connecting part 29 of the light guide plug 25 of the endoscope body 21 is connected to the light guide socket 41 of the light source apparatus 40. Also, the imaging signal plug 54 provided at the tip of the imaging signal cord 53 of the imaging controlling apparatus 50 is connected to the imaging signal socket 30 provided on the above mentioned light guide plug 25.

In the thus connected state, when the lamp 42 of the above mentioned light source apparatus 40 is made to emit a light, the illuminating light emitted from this lamp 42 will pass through the diaphragm 43 and condenser lens 44, will enter the entrance end of the light guide 35 connected to the light guide connecting part 29 of the above mentioned light guide plug 25, will be led to the tip part of the insertable part 22 by the above mentioned light guide 35, will be emitted out of the exit end of this light guide 35 and will be radiated to an object through the light distributing lens 34.

The returning light from the object by this illuminating light will be made to form an image on the solid state imaging device 36 by the objective lens system 33. This solid state imaging device 36 is connected to the signal processing circuit 60 within the above mentioned imaging controlling apparatus 50 through the imaging signal cable 37 within the endoscope body 21 and the imaging signal cable 61 within the imaging signal cord 53 and will be driven by this signal processing circuit 60. The output signal of the above mentioned solid state imaging device 36 will be input into the above mentioned signal processing circuit 60 and will be processed to be a video signal. The video signal produced by this signal processing circuit 60 will be input into the observing monitor 70 so that the object image may be observed by this observing monitor 70.

The operating part switch 38 provided on the operating part 23 of the endoscope body 21 is connected to the signal processing circuit 60 within the above mentioned imaging controlling apparatus 50 through the switch cable 39 within the endoscope body 21 and the switch cable 62 within the imaging signal cord 53 and can make such control as freezing the image of the above mentioned signal processing circuit by the above mentioned operating part switch 38.

The light adjusting signal from the signal processing circuit 60 within the above mentioned imaging controlling apparatus 50 will be input into the diaphragm controlling circuit 45 within the light source apparatus 40 through the light adjusting signal cable 63 within the imaging signal cord 53 and the light adjusting signal cable 65 within the light guide plug 25 and the diaphragm 43 will be controlled with this light adjusting signal.

Now, the endoscope inspection by using the endoscope apparatus 20 of this embodiment is made, for example, as follows.

First of all, a paramedical staff will bring a washed endoscope body 21 to the light source apparatus 40 and imaging controlling apparatus 50. In such case, the paramedical staff will hold the operating part 23 and insertable part 22 near the tip with one hand and will hold the light guide plug 25 with the other hand. While holding the operating part 23 and insertable part 22 with one hand, he will connect the above mentioned light guide plug 25 to the light guide socket 41 of the above mentioned light source apparatus 40 with the other hand and will then connect the imaging signal plug 54 to the imaging signal socket 30 with the hand not holding the operating part 23 and insertable part 22.

Then, the paramedical staff will hand the operating part 23 and insertable part 22 over to a doctor who will make an endoscope inspection. When the inspection ends, the doctor will hand the operating part 23 over to the paramedical staff. As the insertable part 22 after the inspection will be polluted, the paramedical staff had better not touch the insertable part 22.

The paramedical staff will hold the operating part 23 with one hand so that the tip of the insertable part may not touch the floor, will first remove the imaging signal plug 54 from the imaging signal socket 30 with the other hand, will then remove the light guide plug 25 from the light guide socket 41 of the light source apparatus 40, will hold the operating part 23 and light guide plug 25 with the respective hands and will carry them to a washing machine. In such case, in order to minimize the polluted parts, the operating part 23 and light guide plug 25 had better not touch the insertable part 22.

As explained above, in this embodiment, the light source apparatus 40 and imaging controlling apparatus 50 and made separate from each other. The light guide plug 25 is provided at the tip of the universal cord 24 and the imaging signal socket 30 is provided on the side of the plug body 28 of this light guide plug 25. The imaging signal plug 54 provided at the tip of the imaging signal cord 53 extended out of the imaging controlling apparatus 50 is to be connected to the above mentioned imaging signal socket 30.

According to this embodiment, though the light source apparatus 40 and the imaging controlling apparatus 50 are separate from each other, extended out of the operating part 23 of the endoscope body 21 is only one universal cord 26. Therefore, when the light guide plug 25 is connected to the light guide socket 41, the imaging signal cord 53 will not swing and, when the endoscope body 21 is washed or carried, the light guide cable and imaging signal cable will not swing and the light guide plug and imaging signal plug will not collide with each other to be broken. The handlability is high and the operatability is improved.

As described above, the light guide plug 25 and imaging signal plug 4 can be fitted and removed simply with one hand and the operatability is high.

Further, in this embodiment, the signal cables 37 and 61 are of the same kind having equal characteristic impedance. The characteristic impedance of the electric contacts 37a and 61a connecting the above mentioned signal cables 37 and 61 with each other is also made equal to the characteristic impedance of the above mentioned signal cables 37 and 61. Therefore, in the connecting part of the signal cables 37 and 61, the signal will not be reflected, the signal waveform will not be deformed, undesired radiation will not be produced and deterioration of the picture quality and the adverse effect on the peripheral electronic devices will be prevented.

Also, in this embodiment, an imaging signal plug hanger 58 is provided so that, when the light guide plug 25 is not connected to the light guide socket 41, the imaging signal plug 54 or imaging signal cord 53 may be hung on the above mentioned imaging signal plug hanger 58. Therefore, when the light guide plug 25 is fitted or removed or when the endoscope body 21 is not used, the imaging signal cord will not swing and the imaging signal plug 54 will not contact the light source apparatus 40 and the panel 51 or keyboard 52 of the imaging controlling apparatus 50 and will not misoperate.

Further, in this embodiment, as the imaging signal plug 54 is fitted or removed through the side of the light guide plug 25 and the direction of removing the imaging signal plug 54 is made substantially at 90 degree with the direction of removing the light guide plug 25, the directions of fitting and removing the imaging signal plug 54 and light guide plug 25 are different from each other so that, at the time of fitting and removing the imaging signal plug 54, the light guide plug 25 will not be pulled out of the light socket 41.

Further, in this embodiment, as the light adjusting signal cable 63 connected to the signal processing circuit 60 within the imaging controlling apparatus 50 is inserted through the imaging signal cord 53 and is connected to the diaphragm controlling circuit 45 within the light source apparatus 40 through the light guide plug 25 and light guide socket 41, it is not necessary to connect the imaging controlling apparatus 50 and light source apparatus 40 with each other through another cord.

Not only the light adjusting signal but also various signals from the light source apparatus 40 or from the imaging controlling apparatus 50 to the light source apparatus 40 may be transmitted and received through the endoscope body 21 and imaging signal cord 53. The various signals are, for example, the lamp 42 flash trigger signal, the lamp 42 extinguishing informing signal, various synchronizing signals, the diaphragm 43 opening state informing signal and the communicating signals between the respective CPU's of the diaphragm controlling circuit 45 and signal processing circuit 60. In such case, in order to reduce the number of the electric contacts to be as few as possible between the endoscope body 21 and light source apparatus 40, various signals should be superimposed on each other.

Also, according to this embodiment, the position relations between the light guide plug 25 and light guide socket 41 and between the imaging signal plug 54 and imaging signal socket 30 can be freely set, the methods of connecting the respective plugs with the sockets can be respectively independently made most adaptable and therefore the fitting and removing durability can be improved to be higher than in a connector arrangement integrating the illumination connector and signal connector.

By the way, the imaging signal cord 53 is provided on the right or left on the front surface of the imaging controlling apparatus 50, on the side surface as in this embodiment or on the back surface so that the operatability of the keyboard and the like of the imaging controlling apparatus 50 may be improved.

As in this embodiment, the imaging signal plug hanger 58 is provided on the side surface of the imaging controlling apparatus 50 on the side on which the above mentioned imaging signal cord 53 is provided so that the imaging signal cord 53 may not be in the way.

The position of the imaging signal socket 30 is not limited to be on the upper side of the light guide plug 25 as illustrated but may be, for example, on the right side so that a right-handed paramedical staff may easily fit and remove the imaging signal socket 54 and water to be fed to various parts may not accidentally enter the imaging signal socket 30 to cause a short circuit.

Here, when the light guide plug 25 is fitted to and removed from the light guide socket 41, the electric contacts 65b and 45a will be fitted and removed simultaneously with the fitting and removing of the light guide. However, the electric contact 65b has so few pins that a large electric contact can be used, no high assembling precision is required and the fitting and removing durability is not a problem. On the other hand, if the light source apparatus and imaging controlling apparatus are integrated with each other, it will eliminate the electric contacts 37a and 39a which have so many pins that the assembling precision and fitting and removing durability will be problems.

Also, as at least one of the light source apparatus 40 and imaging controlling apparatus 50 is sealed, the influence of noise between the light source apparatus 40 and imaging controlling apparatus 50 can be prevented.

Now, the solid state imaging apparatus to be used for the endoscope apparatus of this embodiment is formed, for example, of a solid state imaging device chip, a substrate mounting this solid state imaging device chip, external leads, bonding wires connecting the above mentioned external leads with bonding pads on the above mentioned chip and a sealing member sealing the above mentioned chips and bonding wires.

Figure 16A:
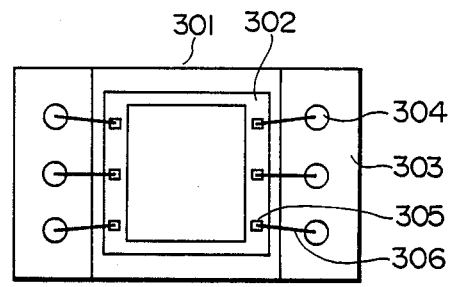
FIG. 16(A) is a plan view of a solid state imaging device.
Figure 16B:
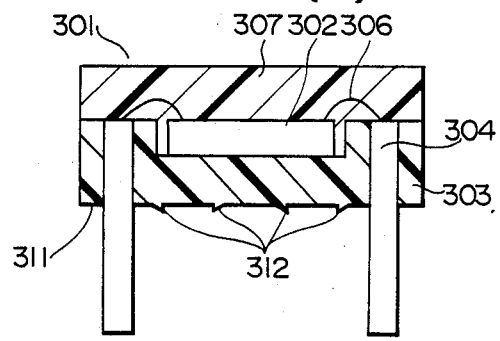
FIG. 16(B) is a sectioned view of the solid state imaging device.

Generally, the substrate mounting the solid state imaging device chip is made mostly of ceramic but a ceramic substrate is so low in dimensional precision that the contour of the solid state imaging apparatus will become substantially large. On the other hand, (as shown, for example, in Japanese patent applications laid open Nos. 58488/1977 and 97322/1979), a substrate made of a molded plastic is known. FIG. 16 shows a solid state imaging apparatus 301 using a plastic molded substrate. FIG. 16(A) is an upper surface view and FIG. 16(B) is a sectioned view. In the system of embedding the external leads 304 in the substrate 303 mounting the solid state imaging device chip 302, the substrate 303 is made by using such molding method as an injection molding method. The solid state imaging device chip 302 is fixed on this substrate 303. Bonding pads 305 on the chip 302 are wire-bonded with the external leads 304 through bonding wires 306 and are covered over with a sealing material 307.

Figure 17:
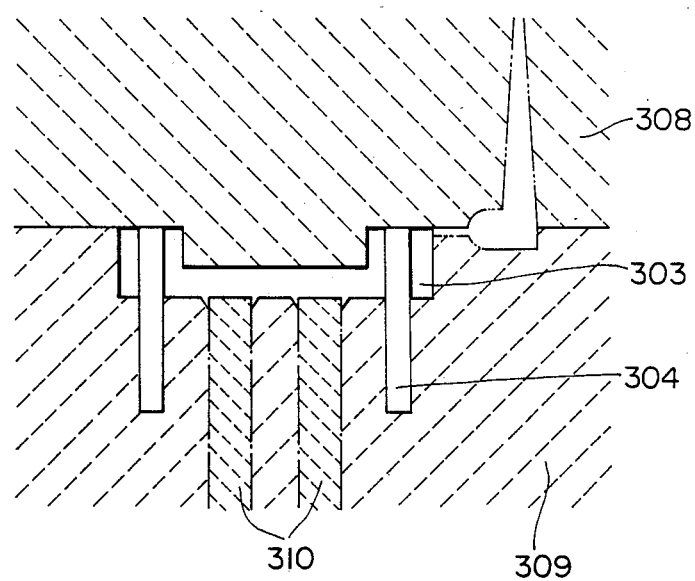

However, in case the substrate 303 is molded in a mold, as shown in FIG. 17, when the substrate 303 is to be taken out of molds 308 and 309 after it is molded, it will be taken out by using push-out points 310 provided within the mold 9. In this case of the shape of this substrate 303, the push-out pin 310 will be set on the bottom surface 311 of the substrate. Therefor, the molding material will enter the clearance between the mold 309 and push-out pin 310, flashes 312 will be produced on the outer edge of the part pushed by the push-out pins 310 of the substrate bottom surface 311 and the substrate bottom surface 311 will no longer remain plane. Generally, in the case of die-bonding or wire-bonding the solid state imaging device 302 with the substrate 30, the substrate bottom surface 311 will have to be positively fixed. However, there are problems that, in such case as is described above, the bottom surface of the substrate will not be kept plane, therefore it will be difficult to positively fix the bottom surface and a positive die-bonding or wire-bonding will not be made.

Therefore, in order to obtain a small solid state imaging apparatus mounting a substrate which can be positively die-bonded or wire-bonded, improved in yield and high in reliability, the following is made.

That is to say, a substrate mounting a solid state imaging device chip and containing external leads is made by molding and in providing a push-out pin for pulling the molding out of the mold on the bottom surface of this substrate, only one main push-out pin trace is made.

A single place is contacted by the main push-out pin of the substrate bottom surface. The greater part of the substrate bottom surface is formed as a plane part and the solid state imaging apparatus is set on the reference plane of the die-bonder or wire-bonder by utilizing this plane part.

Five examples of the solid state imaging apparatus shall be explained in the following on the basis of the drawings. FIGS. 4 to 10 are views showing the first example of the solid state imaging apparatus. A solid state imaging apparatus 320 is made by mounting signal phase-driven solid state imaging device chip 321 on a substrate 322 formed of such molding material as heat-proof plastic material, for example, a glass-embedded epoxy resin or polyamide resin or an injection molding glass. This substrate 322 is provided with a plurality of external leads 323 made of a metal as embedded at the time of molding. The external leads 323 are formed of two kinds of leads different in length. The longer external lead is bent inward to be crank-like. A die-attachment 324 made of a metal is provided between the above mentioned chip 321 and substrate 322 to act as a gland giving a reference potential of the solid state imaging apparatus 320. The die-attachment 324 contacts with a back surface metallized part 326 on the substrate bottom surface 325 through the side surface of the substrate 322 and further with one of the external leads 323. In the metallized part 326 from the side surface to the back surface, the substrate 322 is formed as somewhat recessed. As shown in FIG. 9, the chip 321 is fixed by die-bonding with a conductive paste 327 on the die attachment 324. A color filter array 329 is secured on the image area 328 of the chip 321 but may not be present for black and white. Further, the bonding pad 330 of the chip 321 and the external lead on the upper surface are connected with each other by wire-bonding with a bonding wire 331 and the substrate 322 is covered over with a sealing member 332. A plane part 333 which is a trace by the main push-out pin at the time of molding occupies the greater part of the substrate bottom surface 325 and fine flashes 334 are made on its outer periphery.

Figure 7:
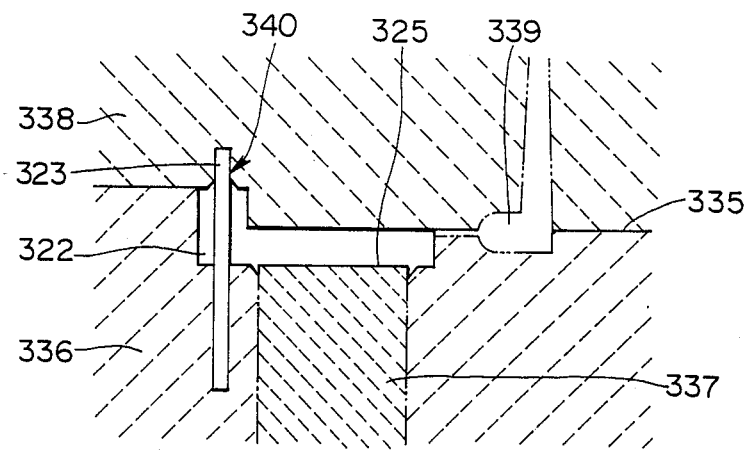

FIG. 7 shows a mold for molding the substrate 322. The mold is formed so that the bottom surface of the substrate 322 may be a parting line 335 and a core mold 336 is provided in one place with a main push-out pin 337 so as to contact the substrate bottom surface 325. The main push-out pin 337 is plane on the end surface and is set to be somewhat smaller in shape and position than the substrate bottom surface and to have an end surface shape as large as possible so as not to interfere with the external leads 323. On the cavity 338 side, a gate 339 which can feed a molding material for forming the substrate 322 is set on the side surface of the substrate. Here, an external lead setting den 340 on the cavity 338 side is somewhat tapered in the inlet so that the external lead 323 may be easily inserted into the setting den 340 when the molds are to be fastened.

In molding the substrate 322, after the molds are fastened so that the external leads 323 may be set in the setting dens 340, a molding material is fed from the gate 339, the molds are separated and the molding is pushed out with the main push-out pin 337.

As formed as in the above, as the main push-out pin 337 is provided on the core mold 336 side on the substrate bottom surface 325, the molding material will enter the fine clearance between the core mold 336 and main push-out in 337 and flashes 334 (minute projections) will be generated on the outer periphery in contact with the main push-out pin 337 on the substrate bottom surface 325 but the plane part 333 formed on the substrate bottom surface 325 by the end surface of the main push-out pin 337 will be a region large enough.

Figure 8A:
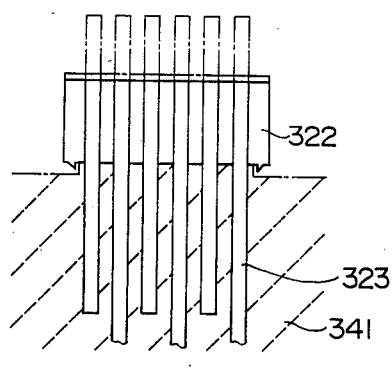
FIG. 8(A) is a side view for explaining the grinding of external leads.
Figure 8B:
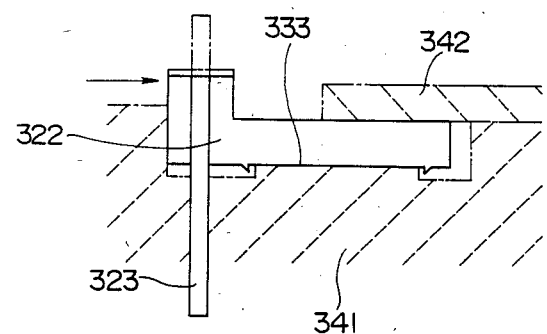
FIG. 8(B) is an elevation for explaining the grinding of the external leads.
Figure 9:
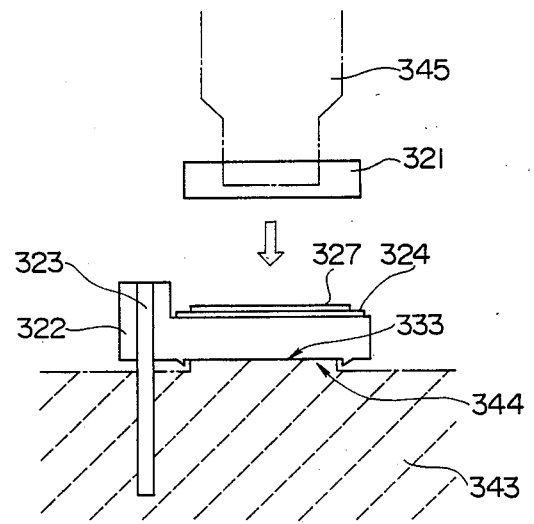

FIG. 8 is a view for explaining the grinding of the upper surfaces of the external leads 323 of the molded substrate. FIG. 8(A) is a side view and FIG. 8(B) is a front view. The external leads 323 are provided extending into the projection on the upper surface of the molded substrate 322. In this part, the substrate 322 is fixed by using a grinding base 341 and substrate presser 342 and the projecting external leads 323 are ground so as to be flush with the molded part of the substrate 322 or to somewhat project. Also, a die-attachment 324 is provided on the substrate 322 and is gold-plated. These works are made by setting the plane 333 in the reference plane of the grinding base 341.

FIG. 9 is a view showing a step of die-bonding the chip 321 on the above mentioned substrate 322. The substrate 322 is set on a reference plane part 344 provided on a die-bonding base 343 by utilizing the plane part 333 on the bottom surface, the die attachment 324 is painted on the surface with a conductive paste 327 and the chip 321 held by a chip holding tool 345 is mounted and fixed on the die attachment 324. Then, the substrate is moved to a wire-bonder and is set on the reference plane by utilizing the plane part 333 in the same manner and the bonding pad 330 and the upper surface of the external leads are wire-bonded with each other through a bonding wire 381.

In the solid state imaging apparatus 320 made by this first example, the chip 321 is of 2.3×2.1 mm., the substrate 322 is of 3×2.3 mm., the external leads 323 are of a diameter of 0.2 mm. and the plane part 333 is of a diameter of 1.8 mm.

According to the above described first example, though the flashes 334 are generated on the outer edge in contact with the main push-out pin 337 of the substrate 322, as the plane part 333 is formed of the end surface of the main push-out pin 337 on the greater part of the substrate bottom surface, at the time of the die-bonding and wire-bonding, the substrate 322 will be able to be positively held, the die-bonding and wire-bonding will be able to be positively made and therefore the yield and reliability of the solid state imaging apparatus will be able to be improved. Also, as the substrate bottom surface is made a reference plane of the solid state imaging apparatus, the parallelism of the chip surface with the substrate bottom surface, of the package surface (sealing member surface) with the substrate bottom surface and of the package surface with the chip surface can be obtained and a solid state imaging apparatus of high precision can be provided. This is very advantageous to directly fitting the package surface to the endoscope tip without leaving a space. thus, the endoscope tip can be made small.

Also, in the work of grinding the bonding pad surface of the external leads 323, the substrate can be fixed to the grinding base 341 by utilizing the plane part 333 and therefore this work can be made positively and easily.

Figure 10:
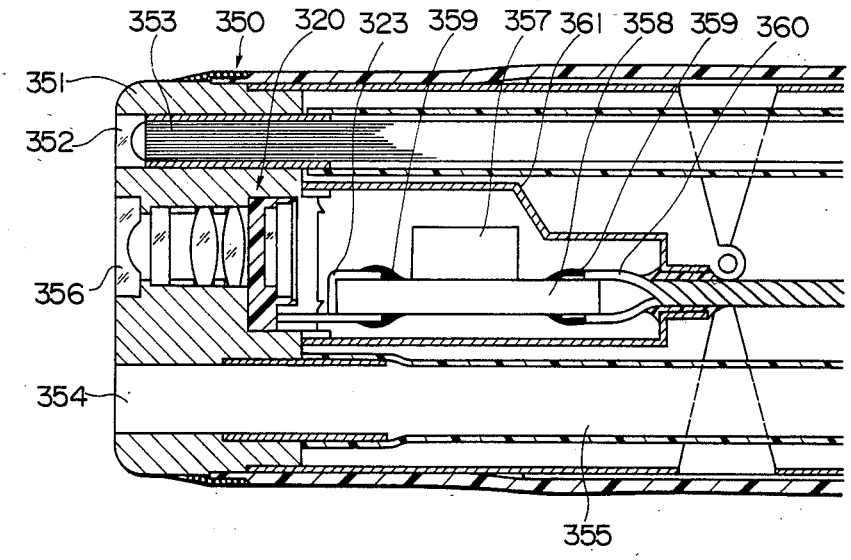

FIG. 10 is a view showing an endoscope tip incorporating the solid state imaging apparatus 320 of the first embodiment. In this endoscope tip part 350, an illuminating lens 352 and illuminating light guide 353 are fixed to a tip forming part body 351, in which a forceps hole 354 is formed. Further, an objective lens 356 is provided and the solid state imaging apparatus 320 is fixed with a bonding agent or the like in the rear of the objective lens 356. The long lead of the rearward extended external leads 323 is bent like a crank and an electrically fitted substrate 358 on which an electric device 357 is mounted is inserted between the long lead and short lead and is fixed with a pattern on the electrically fitted substrate 358 by soldering 359. A cable 360 is fixed by soldering 359 to the pattern at the other end of the electrically fitted substrate 358. The reference numeral 361 represents a shield cover. Here, a part of the cable 360 may be connected directly to the external leads 323.

The other external fittings as of an endoscope are the same as of the known endoscope.

Figure 11A:
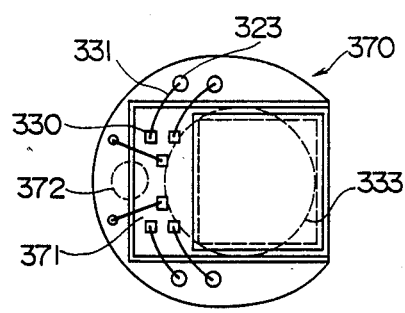
FIGS. 11(A) and (B) relate to the second example of the solid state imaging device.
Figure 11B:
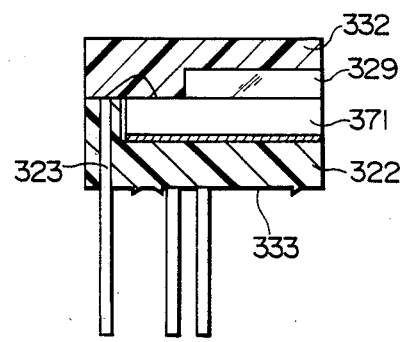
FIG. 11(B) is a sectioned view of the solid state imaging device.

FIG. 11 is a view showing the second example of the solid state imaging apparatus. FIG. 11(A) is an upper surface view. FIG. 11(B) is a sectioned view. This second example is a modification of the first example. The same members as of the first example shall bear the same reference numerals and shall not be explained.

In the solid state imaging apparatus 370 of this second example, the bonding pads 330 of the chip 371 are connected on one side of the chip and the external leads 323 are provided on three sides of the chip 371. Not only a main push-out pin but also an auxiliary push-out pin is provided on the bottom surface of the substrate 322. A plane part 333 as a trace of the push-out pin and a trace 372 made by the auxiliary push-out pin are provided.

By the way, the push-out pin trace which can be a reference surface in such after-step as die-bonding shall be called a main push-out pin trace. Not only the main push-out pin but also an auxiliary push-out pin smaller in size than the main push-out may be properly provided as required. Irrespective of whether the auxiliary push-out pin is provided or not, the main push-out pin trace may be as large as possible and may be provided in a position overlapping the solid state imaging device chip as much as possible.

Figure 12A:
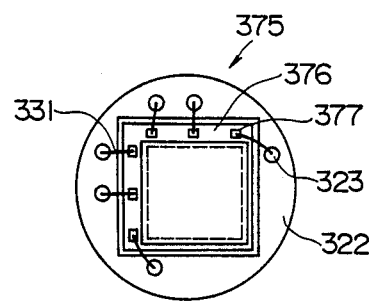
FIGS. 12(A) and (B) relate to the third example of a solid state imaging device.
Figure 12B:
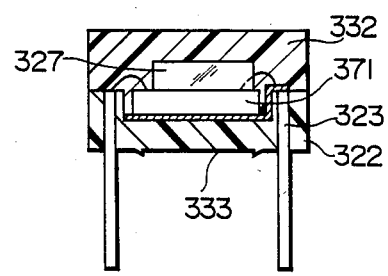
FIG. 12(B) is a sectioned view of the solid state imaging device.

FIG. 12 is a view showing the third example of the solid state imaging apparatus. FIG. 12(A) is an upper surface view. FIG. 12(B) is a sectioned view. In this solid state imaging apparatus 375, the bonding pads 377 on the chip 376 are provided on two perpendicularly intersecting sides and the external leads 323 are provided on four sides. The others are the same as in the first example.

Figure 13A:
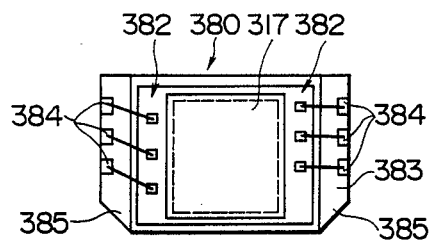
FIG. 13(A) is a plan view of the solid state imaging device.
Figure 13B:
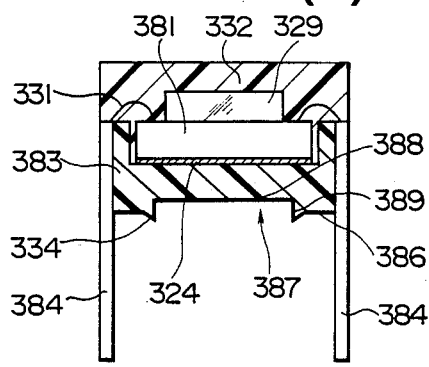
FIG. 13(B) is a sectioned view of the solid state imaging device.

FIG. 13 is a view showing the fourth example of the solid state imaging apparatus. FIG. 13(A) is an upper surface view. FIG. 13(B) is a sectioned view. In the solid state imaging apparatus 380, for the solid state imaging device chip 381, bonding pad rows 382 are provided on the opposite sides and the external lead 384 rows are provided also on the opposite sides. This external lead 384 is square pillar-like and is made to be exposed on the side surface of the substrate 83. A chamfered part 385 is formed in a part following the external lead row of the substrate 383 to make the contour small. On the bottom surface 386 of the substrate 383, a recessed part 387 is formed of recessed part plane 388 and inner peripheral surface 389 of the recessed part. The other formations are the same as in the first example. Therefore, the same reference numerals are used and the explanation shall be omitted.

Figure 14:
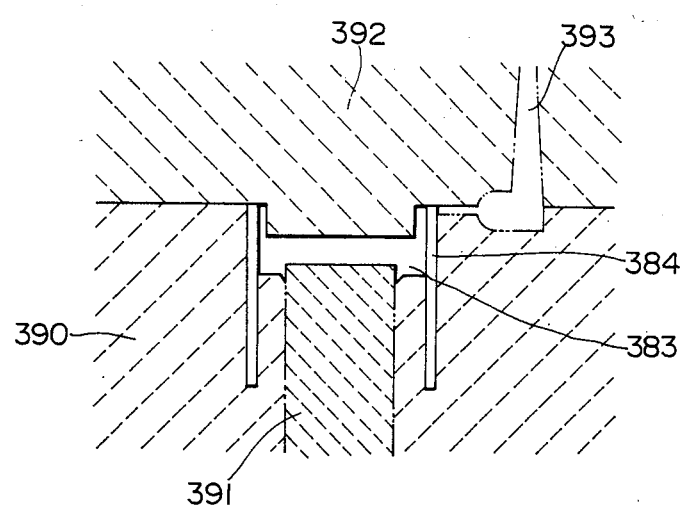

FIG. 14 is a view showing a molding mold for molding the substrate 383. In a core mold 390, a main push-out pin 391 forming the recessed part 387 is set in a position not interferring with the external leads 384 and is provided as slightly projected. A gate 393 is provided on the cavity 392 side. At the time of assembling the solid state imaging apparatus 380, the apparatus is held by utilizing the recessed part plane 388 and inner peripheral surface 389 and is die-bonded and wire-bonded.

According to this fourth example, as the solid state imaging apparatus can be held with both of the recessed part plane 388 and inner peripheral surface 389 as reference surfaces, more positive fixing will be able to be secured and the die-bonding and wire bonding will be more positive.

Figure 15:
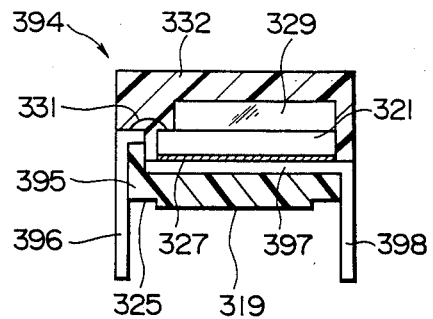
FIG. 15 is a sectioned view of the fifth example of a solid state imaging device.

FIG. 15 is a sectioned view showing the fifth example of the solid state imaging apparatus. In the solid state imaging apparatus 394, the external leads 396 contained in the substrate 395 are made inverted L-like so that the wire bonding surface on thee upper surface of the substrate 395 may be wider. The die attaching member 397 is simultaneously insert-molded and a GND lead 398 is also formed simultaneously downward from the side surface of the substrate 395. Further, a plane part 319 is formed as projected on the bottom surface 325 of the substrate 395.

The other formations are the same as in the first embodiment, shall bear the same reference numerals and shall not be explained.

By the way, the substrate can be made by an injection molding method, casting method or compression molding method. Thus, according to the first to fifth examples, by the large plane part provided on the bottom surface of the substrate, at the time of die-bonding and wire-bonding, the substrate will be able to be positively held and the die-bonding and wire-bonding will be able to be positively made. Thus, a small solid state imaging apparatus high in reliability can be made.

Figure 18:
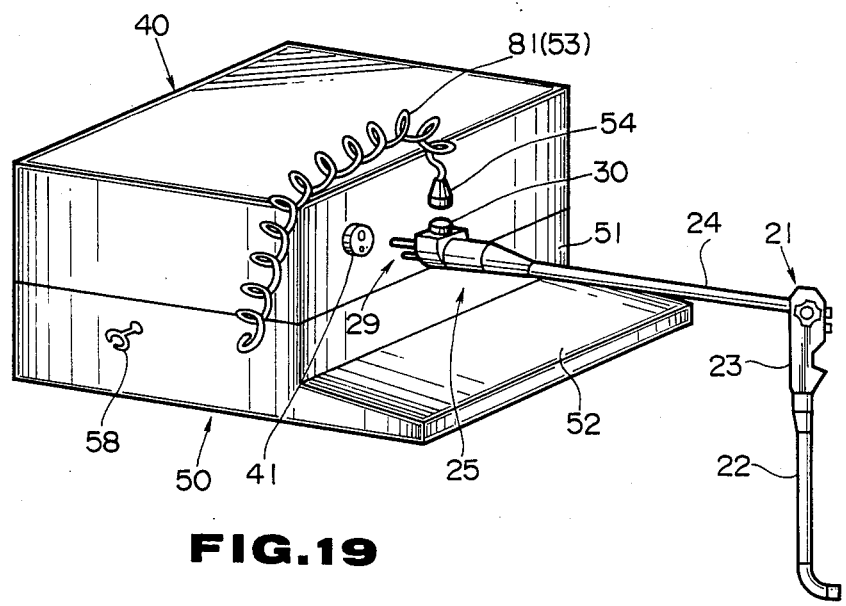
FIG. 18 is a perspective view of an endoscope apparatus of the second embodiment of the present invention.

FIG. 18 shows the second embodiment of the present invention.

In this embodiment, the imaging signal cord 53 is made an extensible curled cord 81. The other formations are the same as in the first embodiment.

According to this embodiment, the imaging signal cord 53 will not be in the way and the operatability will be improved.

By the way, the above mentioned imaging signal cord 53 may be extended out of the back surface of the imaging controlling apparatus.

Figure 19:
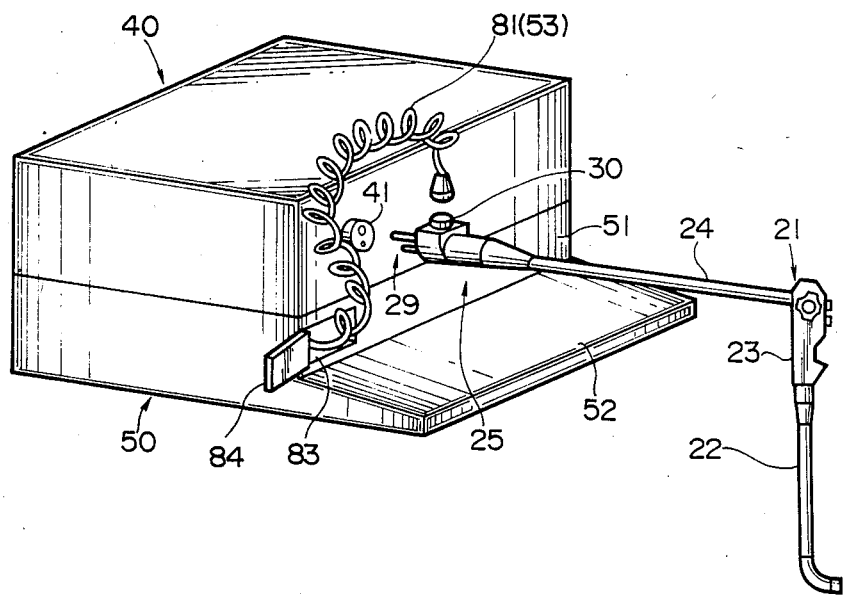
FIG. 19 is a perspective view of an endoscope apparatus of the third embodiment of the present invention.

FIG. 19 shows the third embodiment of the present invention.

In this embodiment, the imaging signal cord 53 is made a curled cord 81 and is extended out of the front surface of the imaging controlling apparatus 50 and its containing part 83 is provided on the front surface of the imaging controlling apparatus 50. A cover 84 free to open and close is provided in the aperture of the above mentioned containing part 83. The other formations are the same as in the first embodiment.

According to this embodiment, when the imaging signal cord 53 is contained in the above mentioned containing part 83 and the cover 84 is closed, the imaging signal cord 53 will not be exposed out of the imaging controlling apparatus 50 and the operatability will be further improved.

By the way, the imaging signal cord 53 may be automatically contained within the containing part 83 by the elasticity of the above mentioned curled cord 81.

Also, the imaging signal cord 53 may not be made a curled cord and a winding apparatus for winding up the imaging signal cord 53 may be provided within the imaging controlling apparatus 50 so that the imaging signal cord 53 may be automatically pulled into the imaging controlling apparatus 50 by this winding apparatus.

FIGS. 20 to 24 show the fourth embodiment of the present invention.

Figure 20:
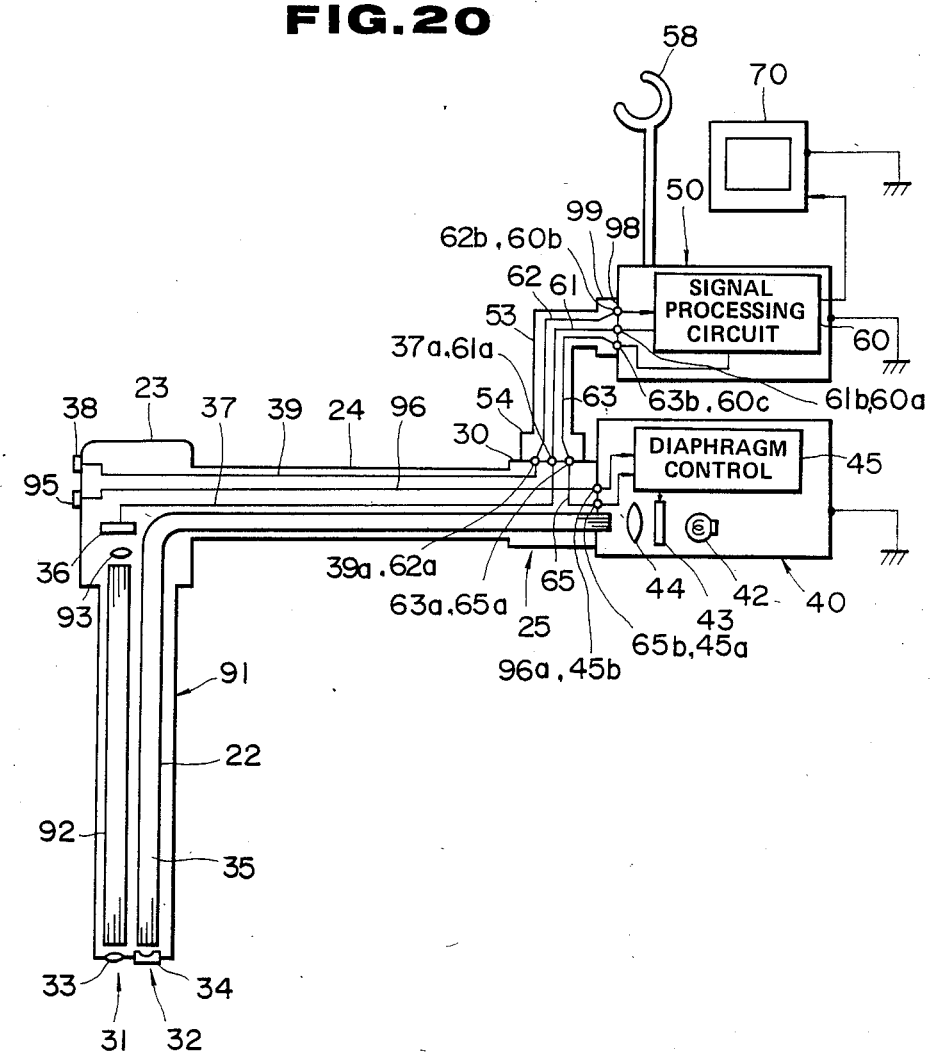
FIGS. 20 to 24 relate to the fourth embodiment of the present invention.

As shown in FIG. 20, the endoscope body 91 in this embodiment is provided within the insertable part 22 with an image guide 92 consisting of a fiber bundle. This image guide 92 is arranged on the tip surface in the image forming position of the objective lens optical system 33 and is led on the rear end into the operating part 23. Within the above mentioned operating part 23, an image forming lens 93 is provided as opposed to the rear end surface of the above mentioned image guide 92 and a solid state imaging device 36 is arranged in the image forming position of this image forming lens 93.

The above mentioned operating part 23 is provided with such switch controlling a light source apparatus 40 as, for example, a switch 95 switching a light adjusting level. A switch cable 96 is connected to this switch 95 and to an electric contact 96a provided in the light guide connecting part 29 of the light guide plug 25, having two pins and connected with an electric contact 45b provided in the light guide socket 41 of the light source apparatus 40 and connected to the diaphragm controlling circuit 45 so that the light adjusting level by the above mentioned diaphragm controlling apparatus 45 may be switched by the above mentioned switch 95. The other formations of the endoscope body 91 are the same as in the endoscope body 21 in the first embodiment.

In this embodiment, the imaging controlling apparatus 50 and imaging signal cord 53 are removably fitted. That is to say, the imaging controlling apparatus 50 is provided with an imaging signal socket 98 and with an imaging signal plug 99 connectable with the above mentioned imaging signal socket 98 at the end on the side opposite to the imaging signal plug 54 of the imaging signal cord 53. The above mentioned imaging signal plug 99 is provided with electric contacts 61b, 62b and 63b connected respectively to signal cables 61, 62 and 63 within the imaging signal cord 53. These electric contacts are provided in the above mentioned imaging signal plug 99 and are connected respectively to electric contacts 60a, 60b and 60c connected to a signal processing circuit 60.

By the way, in this embodiment, the endoscope body may be the endoscope body 21 wherein the solid state imaging device 36 is provided in the tip part of the insertable part 22 as in the first embodiment.

In this embodiment, the same as the first embodiment, signal cables of the same kind are used for the imaging signal cables 37 and 61 and the characteristic impedances of the imaging signal cables 37 and 61 and electric contacts 37a and 61a are all made equal. Further, the characteristic impedances of the electric contacts 61b and 60a connecting the above mentioned imaging signal cable 61 and signal processing circuit with each other are made equal to the characteristic impedances of the above mentioned imaging signal cables 37 and 61. Within the imaging controlling apparatus 50, the kind of signal cable connecting the above mentioned electric contact 60a and the signal processing circuit 60 with each other is made the same as that of the above mentioned imaging signal cables 37 and 61. In the imaging signal transmitting path, all the characteristic impedances are made equal.

Figure 22:
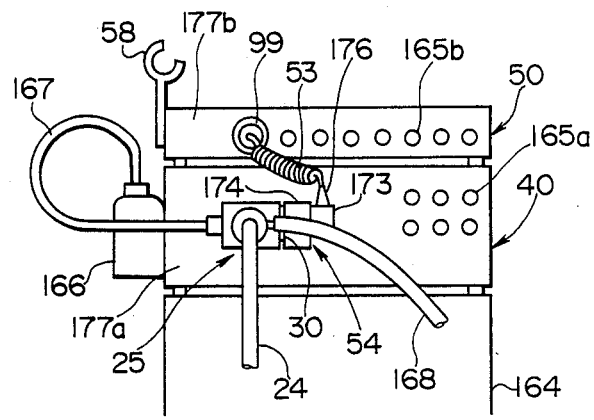
Figure 23:
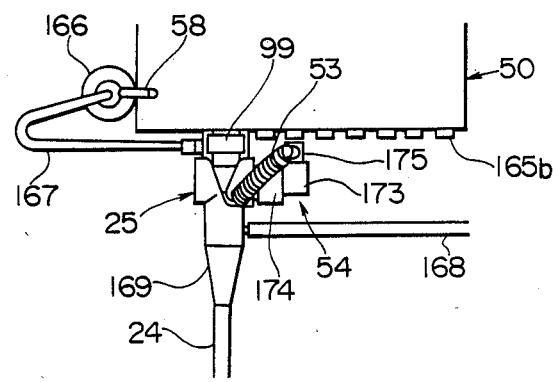
Figure 24:
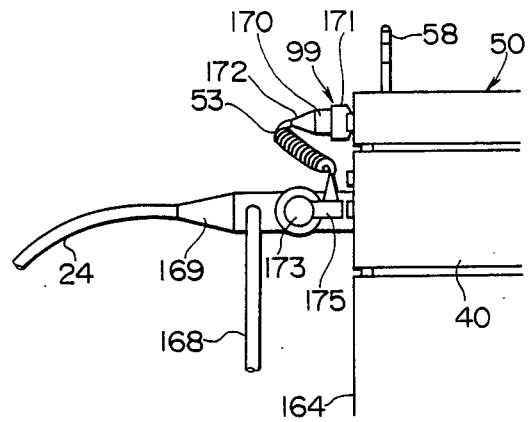

Now, the connecting parts of the endoscope body 91, light source apparatus 40 and imaging controlling apparatus 50 in this embodiment are as shown in FIGS. 22 to 24.

As shown in FIG. 22, the light source apparatus 40 is mounted on the base 164 and the imaging controlling apparatus 50 is mounted on this light source apparatus 40. Many push-in switches 165a and 165b are provided respectively on the front surface panel 177a and 177b of the above mentioned light source apparatus 40 and imaging controlling apparatus 50, respectively. As the imaging controlling apparatus 50 is thus mounted on the light source apparatus 40, it is easy to operate the switch 165b of the imaging controlling apparatus 50. The monitor 70 may be mounted on the imaging controlling apparatus 50. In such case, the imaging signal plug hanger 58 is provided at the left side of the imaging controlling apparatus 50 so as not to obstruct viewing the monitor 70. The light guide socket 41 (shown in FIG. 1) to which the light guide plug 25 is connected is arranged on the left side of the front surface panel 177a of the light source apparatus 40. The above mentioned switches 165a are arranged on the right side of the front surface panel 177a as separate from the above mentioned light guide socket 41. Therefore, it is easy to operate the switches 165a.

The light guide plug 25 can be linearly fitted to and removed from the light guide socket 41 of the above mentioned light source apparatus 40. Though not illustrated, a detent clicking mechanism is provided between the light guide socket 41 and light guide plug 25.

As seen from the front surfaces of the front panels 177a and 177b, the imaging signal socket 30 is provided on the right side of the above mentioned light guide plug 25 so that the imaging signal plug 54 may be fitted and removed from the right side. The above mentioned imaging signal plug 54 is provided with a cam ring 174 so that, when this cam ring 174 is rotated, by the operation of a cylindrical cam, the imaging signal plug 54 may be removably fitted to the imaging signal socket 30.

As shown in FIG. 23, the body 173 of the imaging signal plug 54 is provided with a projection 175 projecting on the light source apparatus 40 side. An imaging signal cord 53 is extended upward through a buckling preventer 176 from this projection 175. As the projection 175 is thus provided, it is easy to rotate the above mentioned cam ring 174. The above mentioned imaging signal cord 53 is a curled cord. The imaging signal plug 99 provided at the end of this imaging signal cord 53 can be linearly fitted to and removed from the imaging signal socket 98 (FIG. 20) provided on the front surface panel 177b of the imaging controlling apparatus 50. As shown in FIG. 24, the above mentioned imaging signal plug 99 is screwed into the above mentioned imaging signal socket 98 by a screwing ring 171.

A sucking tube 168 is connected on the right side of the above mentioned light guide plug 25 and on the front side of the above mentioned imaging signal plug 54. The projection 175 of the imaging signal plug 54 and the sucking tube 168 are arranged on opposite sides of the body 173. Thus, as the removably fitting directions of the imaging signal plug 54 and sucking tube 168 are the same, either of the imaging signal plug 54 and sucking tube 168 may be first fitted or removed easily.

A water feeding tube 167 is removably fitted to the above mentioned light guide plug 25 from the left side and is connected at the other end to a water feeding tank 166 fitted to the left side of the light source apparatus 40. As the imaging signal socket 30 is thus arranged on the side opposite the water feeding tube 167, even if water jets out of the water feeding tube 167, it will be prevented from entering the imaging signal socket 30.

By the way, though not illustrated, a sucking channel and water feeding channel communicating respectively with the above mentioned sucking tube 168 and water feeding tube 167 are provided within the insertable part 22, operating part 23 and universal cord 24.

Figure 21:
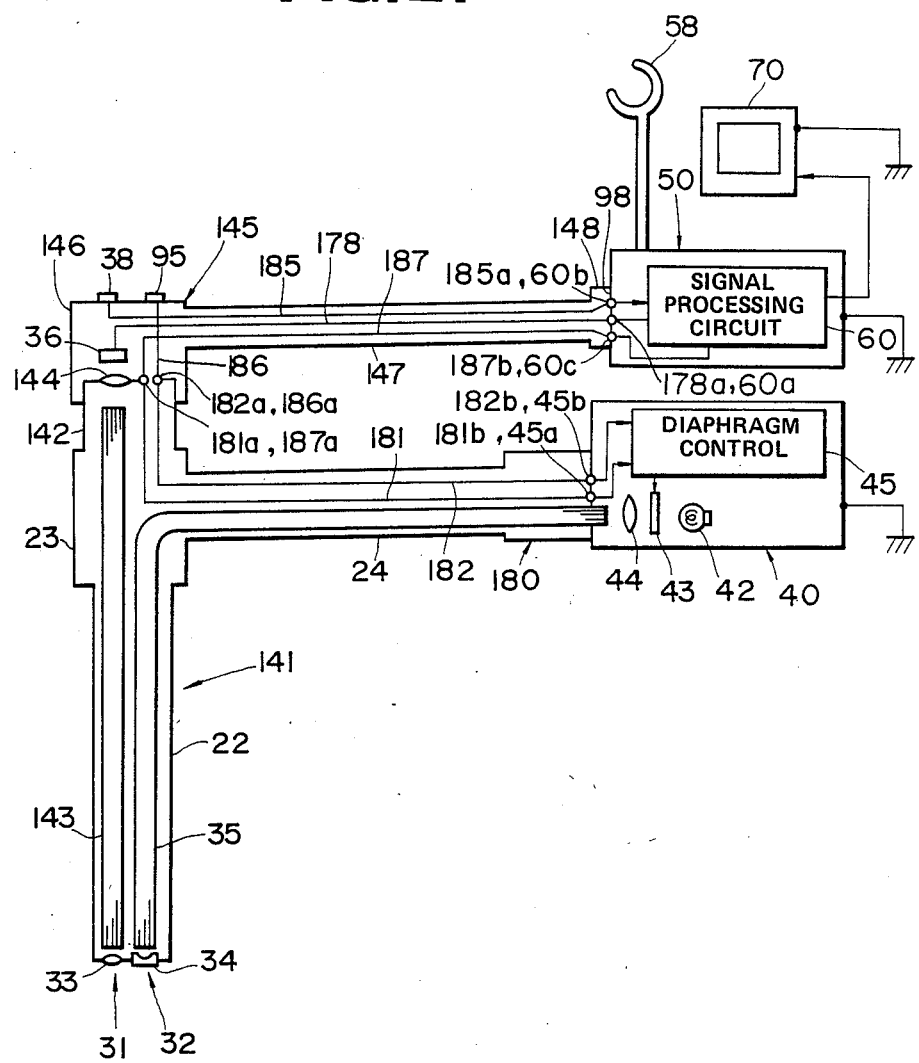

By the way, in this embodiment, as shown in FIG. 21, the fiber scope 141 and externally fitted television camera 145 can be also connected to the above mentioned light source apparatus 40 and imaging controlling apparatus 50.

The above mentioned fiber scope 141 has an eyepiece part 142 at the rear end of the operating part 23. An image guide 143 consisting of a fiber bundle is provided within the insertable part 22 and is arranged on the tip surface in the image forming position of the objective optical system 33 and on the rear end surface opposite to an eyepiece lens 144 provided in the above mentioned eyepiece part 142 so that an object image transmitted by the above mentioned image guide 143 through the above mentioned eyepiece lens 144 may be observed by a naked eye. The above mentioned eyepiece part 142 is provided with two electric contacts 181a and 182a to which signal cables 181 and 182 are respectively connected. These signal cables 181 and 182 are inserted through the operating part 23 and universal cord 24 and are connected respectively to electric contacts 181b and 182b provided in a light guide plug 180 connected to the light source apparatus 40. The above mentioned electric contacts 181b and 182b are connected respectively to electric contacts 45a and 45b connected to a diaphragm controlling circuit 45 within the above mentioned light source apparatus 40.

The same as in the endoscope body 21 of the first embodiment, a light distributing lens 34 is arranged in the tip part of the above mentioned insertable part 22 and a light guide 35 is provided on the rear end of this light distributing lens 34, is inserted through the above mentioned insertable part 22 and universal cord 34 and is extended to the light guide plug 180.

On the other hand, the above mentioned television camera 145 has a camera head 146 and a camera cord 147 extended from this camera head 146 and provided in the tip part with an imaging signal plug 148 connected to the imaging signal socket 98 of the imaging controlling apparatus 50. The above mentioned camera head 146 is to be removably connected to the eyepiece part 142 of the above mentioned fiber scope 141 and has a solid state imaging device 36 arranged in the image forming position of the above mentioned eyepiece lens 144 which is also a photographing lens. An imaging signal cable 178 is connected to this solid state imaging device 36, is inserted through the above mentioned camera cord 147 and is connected to an electric contact 178a of the above mentioned imaging signal plug 148.

The above mentioned camera head 146 is provided with a switch 38 or making such control as frame freezing and a switch 95 switching a light adjusting level or the like. A switch cable 185 is connected to the above mentioned switch 38, is inserted through the above mentioned camera cord 147 and is connected to an electric contact 185a of the above mentioned imaging signal plug 148. A switch cable 186 is connected to the above mentioned switch 95 and is connected to an electric contact 186a connected to an electric contact 182a of the above mentioned eyepiece part 142. Further, the above mentioned camera head 146 is provided with an electric contact 187a connected to an electric contact 181a of the above mentioned eyepiece part 142. A signal cable 187 is connected to this electric contact 187a, is inserted through the above mentioned camera cord 147 and is connected to an electric contact 187b of the above mentioned imaging signal plug 148. The electric contacts 178a, 185a and 187b provided in the above mentioned imaging signal plug 148 are to be connected respectively to the electric contacts 60a, 60b and 60c of the imaging signal socket 98 of the imaging controlling apparatus 50. The above mentioned electric contact 187a is to be connected to the electric contact 181a of the above mentioned eyepiece part 142.

By the way, in the above mentioned television camera 145, the imaging signal cable 178 is of the same kind having equal characteristic impedance to the of the imaging signal cable 37 within the endoscope body 91 and the imaging signal cable 61 within the imaging signal cord 53. Also, the characteristic impedance of the electric contacts 178a and 60a connecting the above mentioned imaging signal cable 178 and signal processing circuit 60 with each other is made equal to the characteristic impedance of the above mentioned imaging signal cable 178, that is, to the characteristic impedance of the imaging signal cables 37 and 61.

Thus, in this embodiment, in case the endoscope body 21 or 91 is used, the imaging signal cord 53 will be used and, in case the fiber scope 141 or television camera 145 is used, the above mentioned imaging signal cord 53 will not be used and the imaging signal plug 148 of the television camera 145 will be connected directly to the imaging signal socket 98 of the imaging controlling apparatus 50. This is because, if the television camera 145 is connected to the imaging controlling apparatus 50 through the imaging signal cord 53, the connecting part of the imaging signal plug 54 with the imaging signal plug 148 will exist between the camera cord 147 and imaging signal cord 53 and will swing to deteriorate the operatability.

According to this embodiment, in the endoscope body 91, as the solid state imaging device 36 is provided within the operating part 23, many pixels can be used for the solid state imaging device 36 and a picture image having high resolution can be obtained.

Also, as the imaging signal cord 53 is removably fitted to the imaging controlling apparatus 50, when this imaging signal cord 53 is not used, if this imaging signal cord 53 is removed from the imaging controlling apparatus 50, this imaging signal cord 53 will not be in the way and the operatability will be improved.

The same as in the first embodiment, as the imaging signal transmitting paths are all made equal in characteristic impedances, in the connecting part or the like of the respective signal cables, no reflection of the signal will be produced no signal waveform will be distorted, no undesired radiation will be produced and deterioration of the picture quality and adverse influence on the peripheral electronic device will be able to be prevented.

Now, the number of times of fitting and removing the endoscope body to and from the light source apparatus 40 and imaging controlling apparatus 50 will be high.

In a hospital using it, for example, 20 times a day, if it is used for 5 days a week and 50 weeks a year, it will be used 5,000 times a year. As the endoscope must be washed each time, it will have to be washed 5,000 times a year.

However, the fitting and removing durability of the electric connector of even a high durability type in which the contacts are gold-plated is only about 500 times and particularly, in the case of handling such feeble current as in a CCD driving signal or video signal, when the fitting and removing are repeated, the contact resistance of the contacts will increase to an extent likely to make the contact bad.

In this embodiment, as the imaging signal cord 53 is replaceable, when the imaging signal socket 30 and the imaging signal plug 54 are found to make poor contact, the imaging signal cord 53 may be replaced with a new one. If the contacts of the imaging signal plug 54 are new, the contact resistance will return to normal.

Figure 31:
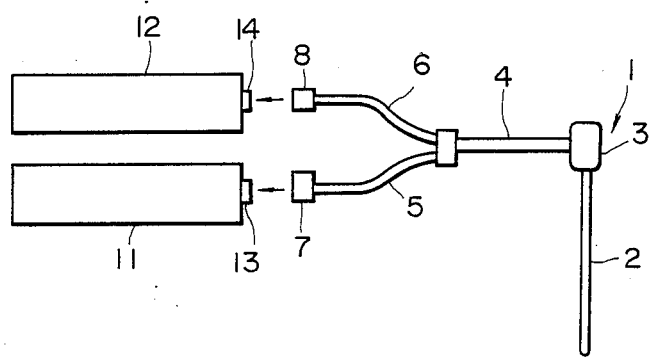
FIGS. 31 and 32 show examples of a related art.
Figure 32:
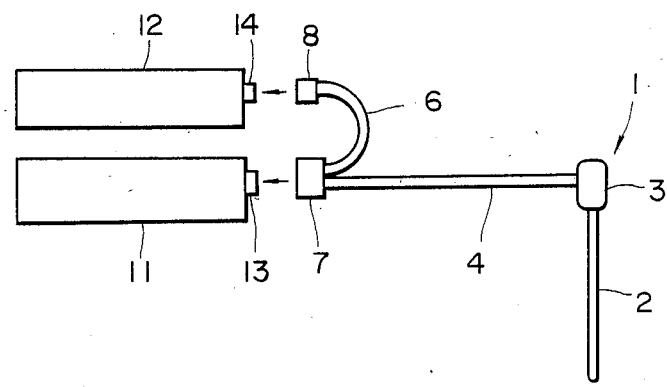

On the other hand, in the examples shown in FIGS. 31 and 32 and the examples disclosed in the gazette of Japanese patent application laid open No. 80429/1985 (U.S. Pat. No. 4,539,586), when the contacts become bad, the endoscope body or imaging controlling apparatus 12 will have to be replaced with a new one which would be uneconomical.

The other formations, operations and effects of this embodiment are the same as in the first embodiment.

Figure 25:
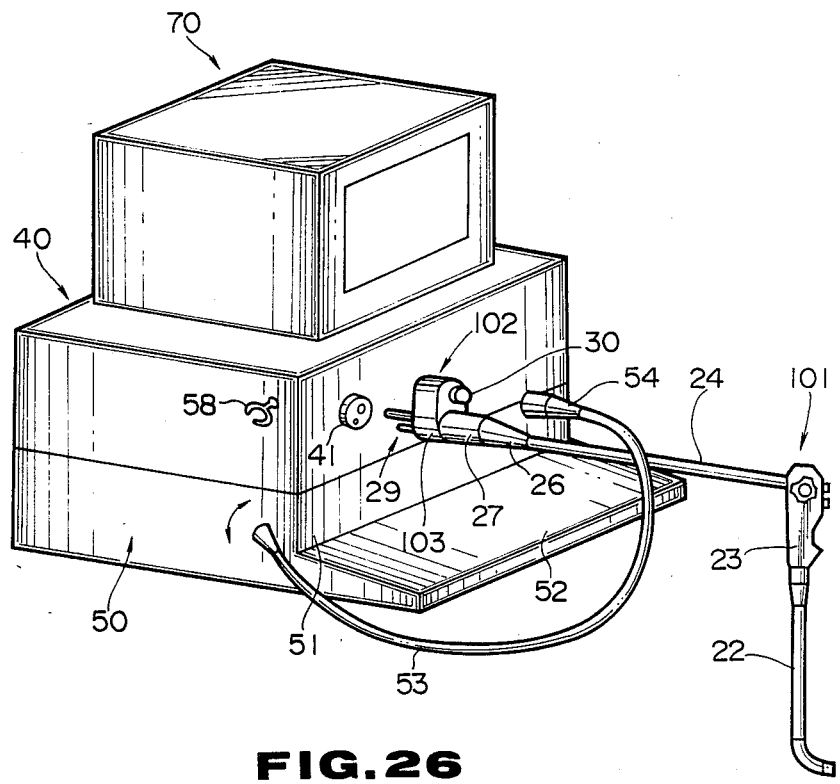
FIGS. 25 to 27 relate to the fifth embodiment of the present invention.
Figure 26:
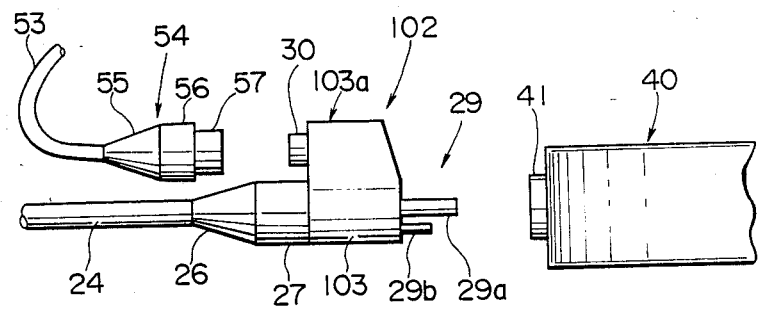
Figure 27:
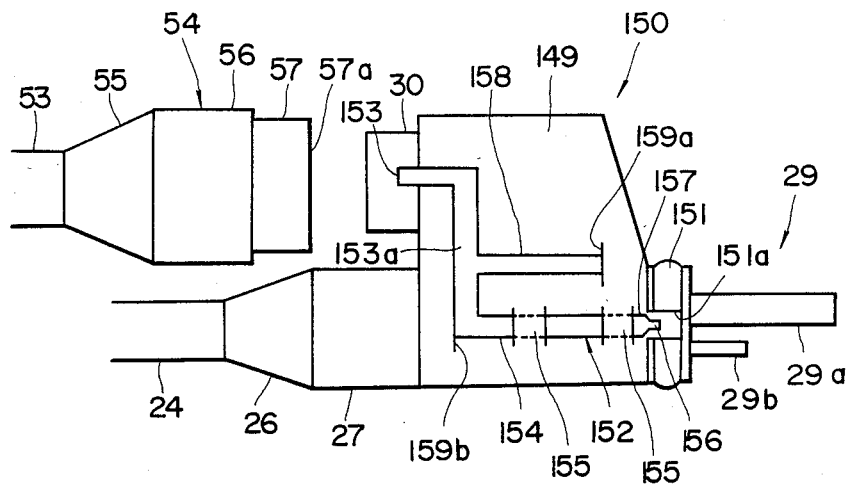

FIGS. 25 to 27 show the fifth embodiment of the present invention.

In this embodiment, the direction of the operation of fitting and removing the imaging signal plug 54 is made the same as the direction of the operation of fitting and removing the light guide plug.

As shown in FIG. 25, a light guide plug 102 is provided at the tip of the universal cord 24 of the endoscope body 101 and is provided with a buckling prevention part 26 tapered to a greater diameter toward the tip, a thick gripping part 27 and a plug body 103 connected in turn to the tip of the above mentioned universal cord 24 as shown in FIG. 26. A light guide connecting part 29 is provided at the tip of the above mentioned plug body 103 formed to be expanded sidewise of the axial direction of the universal cord 24. An imaging signal socket 30 is provided at the rear end (on the universal cord 24 side) of this expanded part 103a so that the direction of the operation of fitting and removing the imaging signal plug 54 may coincide with the direction of the operation of fitting and removing the light guide plug 102.

By the way, when the imaging signal plug 54 is to be pulled out of the imaging signal socket 30, the buckling prevention part 55 and gripping part 56 of the above mentioned imaging signal plug 54 will be gripped and, when the light guide plug 102 is to be pulled out of the light guide socket 41, the buckling prevention part 26 and gripping pat 27 of the above mentioned light guide plug 102 will be gripped.

In this embodiment, the force (which shall be mentioned as a pull-out force) required to pull the light guide plug 102 out of the light guide socket 41 is set to be larger than the pull-out force required to pull the imaging signal plug 54 out of the imaging signal socket 30. Therefore, in case the light guide plug 102 is connected to the light guide socket 41 and the imaging signal plug 54 is connected to the imaging signal socket 30, when the imaging signal plug 54 is to be pulled out of the imaging signal socket 30, the light guide plug 102 will not be pulled out of the light guide socket.

The connecting part of the imaging signal cord 53 with the imaging controlling apparatus 50 is made rotatable with respect to the imaging controlling apparatus 50 to improve the operability of the imaging signal cord 53.

The imaging signal plug hanger 58 is provided on the side of the light source apparatus 40 on the same side as imaging signal plug hanger 58 instead of the imaging controlling apparatus 50.

The other formations are the same as in the first or fourth embodiment.

According to this embodiment, as the direction of the operation of fitting and removing the imaging signal plug 54 is made the same as the direction of the operation of fitting and removing the light guide plug 102, when the imaging signal plug 54 is fitted to and removed from the imaging signal socket 30, no swinging force will be applied to the connecting part of the light guide socket 41 with the light guide plug 102 and the connecting part of the light guide socket 41 with the light guide plug 102 will become hard to break.

By the way, when the connecting force (or pull-out force) of the light guide socket 41 with the light guide plug 102 is smaller than the pull-out force between the imaging signal plug 54 and the imaging signal socket 30 provided on the above mentioned light guide plug 102, the following modification may be made.

That is to say, the imaging signal plug 54 may be connected with the imaging signal socket 30 through a pin plug in which the internal electric contacts themselves are in the direction parallel with the connecting direction and a removably fitting mechanism by a screw or bayonet may be provided outside. In such case, when the imaging signal plug 54 is to be pulled out of the imaging signal socket 30, the imaging signal plug 54 will be pulled out a little by the screw or bayonet until the internal electric contacts are pulled out and the pulling force becomes small and then will be pulled out straight.

Also, a type of connection wherein the electric contacts of the imaging signal plug 54 and imaging signal socket 30 are displaced in the lateral direction (or rotating direction) may be used. In this case, in the step of connecting the imaging signal plug 54 with the imaging signal socket 30, the electric contacts will not contact each other and therefore the connecting force will be very light. After the connection, as by rotating a lever provided on the imaging signal plug 54 or light guide plug 102, the contacts of either of the imaging signal plug 54 and imaging signal socket 30 will be displaced in the lateral direction and will be connected with each other. In electric contacts of this type, at the time of removing the plug, first of all by operating the lever, the contacts will be pulled and separated in the lateral direction and therefore the pull-out force will be very small. Therefore, in the case of pulling the imaging signal plug 54 out of the imaging signal socket 30, the light guide plug 102 will not be pulled out of the light guide plug 41.

Such mechanism for preventing the light guide plug 102 from being pulled out of the light guide socket 41 when the imaging signal plug 54 is to be pulled out of the imaging signal socket 30 as, for example, a locking mechanism for locking the light guide plug 102 and light guide socket 41 to be connected with each other may be provided.

An example of such locking mechanism is shown in FIG. 27.

A C-ring 151 is fitted to the base part of the light guide connecting part 29 of the same light guide plug 150 as the above mentioned light guide plug 102 so that the light guide plug 150 may be removably fixed to the light guide socket 41 by this C-ring 151.

The plug body 149 of the above mentioned light guide plug 150 is provided with a C-ring deformation preventing member 152 having a pushed-in part 153 projecting on the imaging signal socket 30 side out of the plug body 149, and a shaft-like spring part 158 and sliding part 154 connected through a connecting part 153a to this push-in part 153. The above mentioned spring part 158 and sliding part 154 are both formed to be parallel with the direction of fitting and removing the light guide plug 150. The above mentioned spring part 158 has a resiliency and is extensible in the axial direction. A narrow part 156 is formed at the tip of the above mentioned sliding part 154.

The above mentioned plug body 149 is integrally provided with sliding guides 15 so that the above mentioned sliding part 154 may move in the axial direction along these sliding guides 155. Also, the above mentioned plug body 149 is integrally provided with a stopper part 159a contacting the tip of the above mentioned spring part 158 and a stopper part 159b contacting the rear end of the above mentioned connecting part 153a.

In the waiting state in which the imaging signal plug 54 is not connected to the imaging signal socket 30, by the work of the spring part 158, the above mentioned C-ring deformation preventing member 152 will be positioned on the left side in the drawing until it contacts the stopper part 159b. By the way, the above mentioned spring part 158 contacts at the right end with the stopper part 159a. In this state, the narrow part 156 of the sliding part 154 is positioned in the clearance (mentioned as the C-ring clearance hereinafter) 151a of the C-ring 151 to prevent the rotation of the C-ring 151. In this state, the width of the above mentioned narrow part 156 is narrower enough than the C-ring clearance 151a, therefore the C-ring 151 is deformable inward (so that the outside diameter may be smaller) and the light guide plug 150 can be connected to the light guide socket 41 of the light source apparatus 40.

On the other hand, after the above mentioned light guide plug 150 is connected to the light guide socket 41 of the light source apparatus 40, when the imaging signal plug 54 is connected to the imaging signal socket 30, by the end surface 57a of the imaging signal connecting part 57 of the imaging signal plug 54, against the energizing force of the spring part 158, the pushed-in part 153 will be pushed in, the C-ring deformation preventing member 152 will be displaced to the right side and the large width part 157 on the rear end side of the narrow part 156 at the tip of the above mentioned sliding part 154 will enter the C-ring clearance 151a. As the width of the above mentioned large width part 157 is formed to be substantially equal to the width of the above mentioned C-ring clearance 151a, in this state, the C-ring 151 can not be deformed and the light guide plug 150 can not be pulled out of the light guide socket 41 of the light source apparatus. Therefore, in the case of pulling the imaging signal plug 54 out of the light guide plug 150, the light guide plug 150 will not be pulled out of the light guide socket 41.

By the way, when the connecting force of the imaging signal socket 30 with the imaging signal plug 54 is made larger than the energizing force of the spring part 158, the imaging signal plug 54 will not be naturally pulled out of the imaging signal socket 30.

When the imaging signal plug 54 is pulled out of the light guide plug 150, the C-ring deformation preventing member 152 will be displaced to the left side and the light guide plug 150 will be able to be pulled out of the light guide socket 41.

In case such locking mechanism as in the above is used, without making any locking operation, when the imaging signal plug 54 is to be pulled out of the imaging signal socket 30, the light guide plug 102 will be able to be prevented from being pulled out and the operatability will be high.

The other operations and effects of this embodiment are the same as in the first or fourth embodiment.

Figure 28:
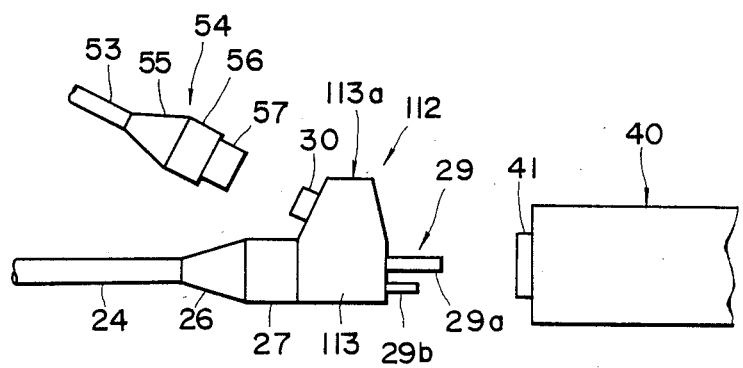
FIG. 28 is a side view showing as magnified a connecting part of an endoscope apparatus of the sixth embodiment of the present invention.

FIG. 28 shows the sixth embodiment of the present invention.

In this embodiment, the same as in the fifth embodiment, the plug body 113 of the light guide plug 112 is formed to be expanded sidewise of the axial direction of the universal cord 24 and an imaging signal socket 30 is provided at the rear end (the end on the universal cord 24 side) of this expanded part 113a so that the direction of the operation of fitting and removing the imaging signal plug 54 may be oblique to the direction of the operation of fitting and removing the light guide plug 112.

Figure 29:
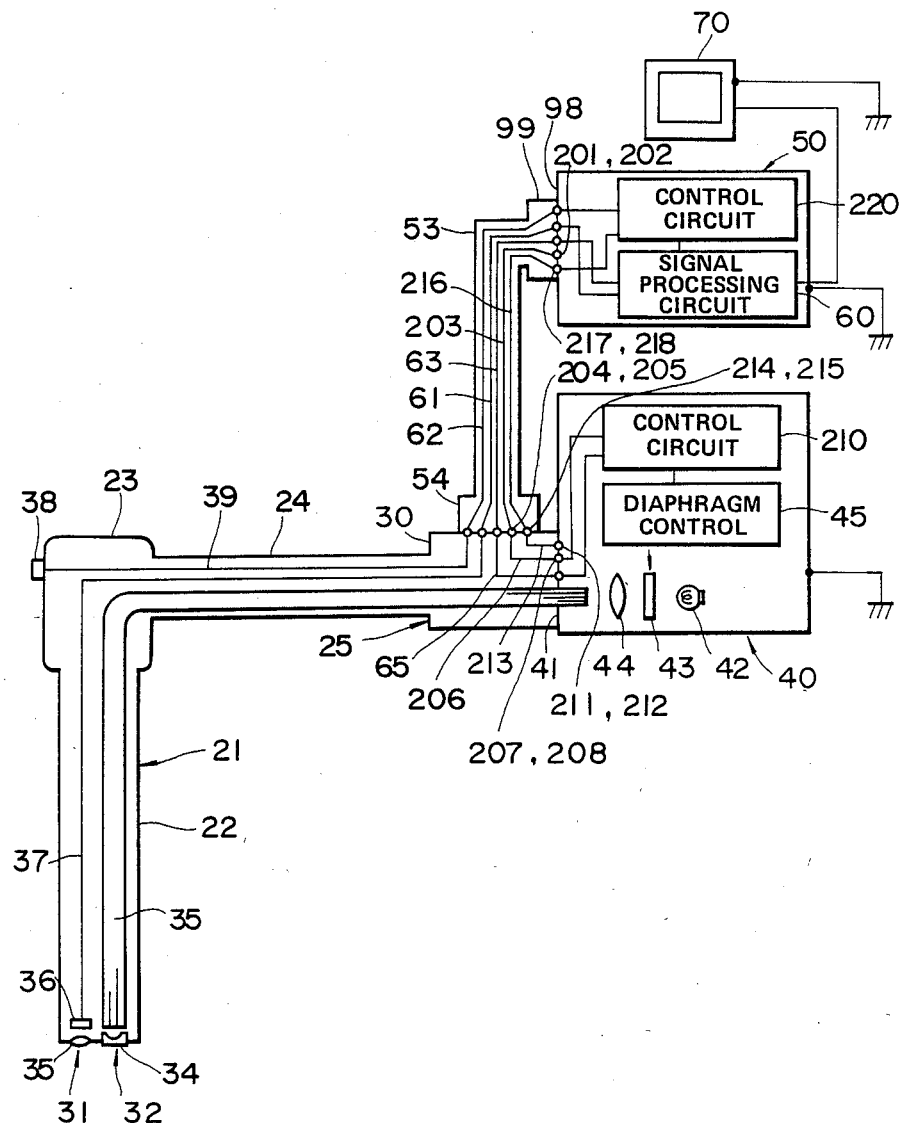
FIGS. 29 and 30 relate to the seventh embodiment of the present invention.
Figure 30:
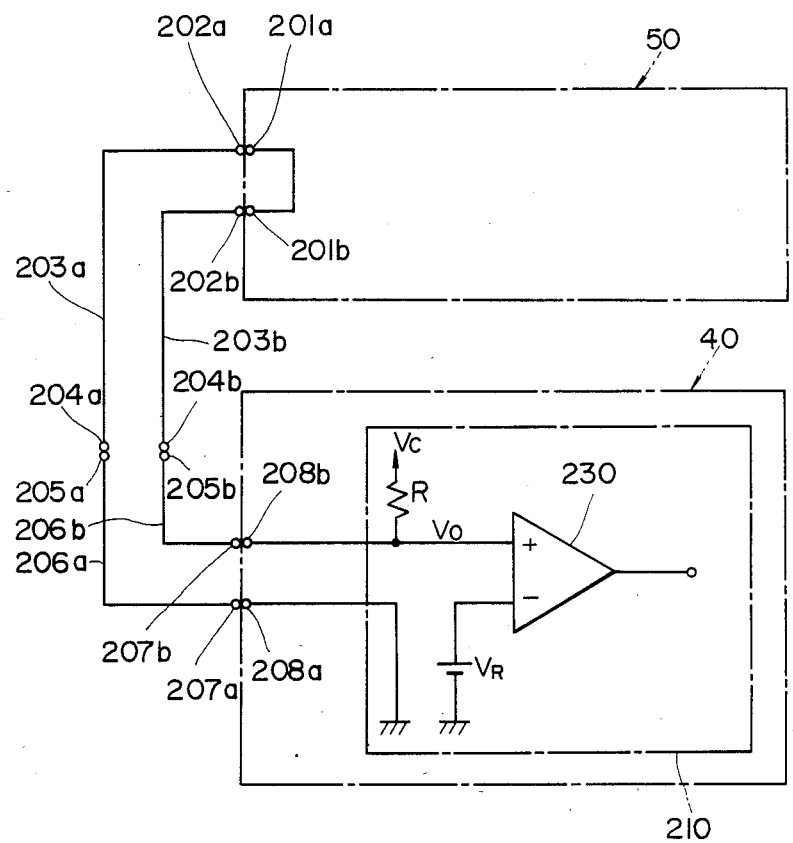

According to this embodiment, as the imaging signal plug 54 is fitted and removed in the direction oblique to the direction of the operation of fitting and removing the light guide plug 112, when the imaging signal plug 54 is to be pulled out of the imaging signal socket 30, the light guide plug 112 will be hard to pull out of the light guide socket 41 and, when the imaging signal plug 54 is to be fitted to and removed from the imaging signal socket 30, the swinging force applied to the connecting part of the light guide socket 41 with the light guide plug 112 will be small and the connecting part of the light guide socket 41 with the light guide plug 112 will be hard to break FIGS. 29 and 30 show the seventh embodiment of the present invention.

In this embodiment, there is provided a means of sensing whether or not the light source apparatus 40 and imaging controlling apparatus 50 are connected with each other through an imaging signal cord 53. By the way, the endoscope body 21 is of substantially the same formation as in the first embodiment and, the same as in the fourth embodiment, the imaging signal cord 53 is removably fitted to the imaging controlling apparatus 50.

As shown in FIG. 29, the imaging signal socket 98 of the imaging controlling apparatus 50 is provided with a fitting and removal detecting contact 201 consisting of two contacts wired within the imaging controlling apparatus 50. Corresponding to the above mentioned contact 201, in the imaging signal cord 53, the imaging signal plug 99 is provided with a contact 202, the imaging signal plug 54 is provided with a contact 204 and both contacts 202 and 204 are connected with each other through a signal cable 203. Also, the imaging signal socket 30 is provided with a contact 205 connected to the above mentioned contact 204 and connected to a contact 207 provided in the light guide connecting part 29 of the light guide plug 25 through a signal cable 206 within the light guide plug 25. The light guide socket 41 of the light source apparatus 40 is provided with a contact 208 connected to the above mentioned contact 207 and connected to a control circuit 210 provided within the light source apparatus 40. It is sensed by this control circuit 210 whether or not the imaging controlling apparatus 50 and imaging signal plug 99; the imaging signal plug 54 and imaging signal socket 30; and the light guide plug 25 and light source apparatus 40 are respectively connected with each other, that is to say, whether or not the light source apparatus 40 and imaging controlling apparatus 50 are connected with each other through the imaging signal cord 53 is sensed.

In the same manner, the light guide socket 41 of the light source apparatus 40 is provided with a fitting and removal detecting contact 211 consisting of two contacts wired within the light source apparatus 40. Corresponding to the above mentioned contact 211, the light guide plug 25 is provided with a contact 212 connected to a contact 214 provided in the imaging signal socket 30 through a signal cable 213 within the light guide plug 25. Corresponding to the above mentioned contact 214, in the imaging signal cord 53, the imaging signal plug 54 is provided with a contact 215, the imaging signal plug 99 is provided with a contact 217 and both contacts 215 and 217 are connected with each other through a signal cable 216. The imaging signal socket 98 is provided with a contact 218 connected to the above mentioned contact 217 and connected to a control circuit 220 provided within the imaging controlling apparatus 50. It is sensed by this control circuit 220 whether or not the light source apparatus 40 and imaging controlling apparatus 50 are connected with each other through the imaging signal cord 53.

By the way, in this embodiment, the electric contact connected to the light adjusting signal cable 65 in the above mentioned light guide socket 41 is connected to the diaphragm controlling circuit 45 through the above mentioned control circuit 210. In case it is sensed by the above mentioned control circuit 210 that the light source apparatus 40 and imaging controlling apparatus 50 are not connected with each other through the imaging signal cord 53, the transmission and reception of electric signals between the light source apparatus 40 and imaging controlling apparatus 50 will be stopped by the above mentioned control circuit 210 and the diaphragm 43 will be completely closed so that no heat ray may be emitted out of the light distributing lens 34 of the endoscope body 210.

The electric contact connected to the switch cable 62 in the above mentioned imaging signal socket 98 is connected to the signal processing circuit 60 through the above mentioned control circuit 220. In case it is sensed by the above mentioned control circuit 220 that the light source apparatus 40 and imaging controlling apparatus 50 are not connected with each other through the imaging signal cord 53, the transmission and reception of the electric signal between the light source apparatus 40 and imaging controlling apparatus 50 and between the endoscope body 21 and imaging controlling apparatus 50 will be stopped by the above mentioned controlling circuit 220.

Thus, in this embodiment, in case the light source apparatus 40 and imaging controlling apparatus 50 are not connected with each other through the imaging signal cord 53, the transmission and reception of electric signals between the light source apparatus 40 and imaging controlling apparatus 50 and between the endoscope body 21 and imaging controlling apparatus 50 will be stopped so that no electricity may flow out of the light source apparatus 40 and imaging controlling apparatus 50 and, even if the electric contacts of the light guide socket 41 and imaging signal socket 98 are touched, no electricity may be felt. Further, the diaphragm 43 is completely closed so that no heat ray may be emitted out of the light distributing lens 34 of the endoscope body 21.

An example of the connection sensing means in the above mentioned control circuit 210 is shown in FIG. 30. The contacts 201, 202, 204, 205, 207 and 208 and the signal cables 203 and 206 in FIG. 29 are represented respectively by the contacts 201a and 201b, 202a and 202b, 204a and 204b, 205a and 205b, 207a and 207b and 208a and 208b and the signal cables 203a and 203b and 206a and 206b in FIG. 16.

A current source voltage $V_C$ is applied through a resistance R to one contact 208b provided in the light guide socket 41 of the light source apparatus 40 and the other contact 208a is earthed. The voltage Vo of the above mentioned contact 208b is applied to the non-inverted input end of a comparator 230 and a reference voltage $V_R$ is applied to the inverted input end of this comparator 230 and is set to be $0 < V_R < V_C$.

In such formation, as shown in FIG. 30, in case the light source apparatus 40 and imaging controlling apparatus 50 are connected with each other through the imaging signal cord 53, $V_C = 0$ and the output of the comparator 230 will be on the L level. On the other hand, in case either of the light source apparatus 40 and imaging controlling apparatus 50 is not connected, $V_o = V_C$ and the output of the comparator 230 will be on the H level. Therefore, whether in the connected state or not will be detected by the output of the above mentioned comparator 230.

The connection sensing means in the control circuit 220 is also the same.

By the way, the voltage applied to the contacts 208 and 218 to detect the fitting and removal is made so feeble as not to be felt even if the contacts are touched by hand. Or else, the contact for detecting the fitting and removal may be of such structure as is not touched by hand from outside.

The other formations, operations and effects are the same as in the first or fourth embodiment.

By the way, the present invention is not limited to the above mentioned respective embodiments. For example, as a means of connecting and releasing the imaging signal plug and imaging signal socket with and from each other, a male screw may be provided on the outer periphery of the imaging signal socket and a ring having a female screw screwing with the above mentioned male screw may be rotatably provided on the outer peripheral side of the imaging signal plug. Thereby, in the case of connecting and removing the imaging signal plug and imaging signal socket with and from each other, the light guide plug will be prevented from being pulled out of the light guide socket and the swinging force will be prevented from being applied to the connecting part of the light guide socket with the light guide plug.

The present invention can be applied not only to the endoscope apparatus in which the light source apparatus and imaging controlling apparatus are separate from each other but also to the endoscope apparatus in which the light source apparatus and imaging controlling apparatus are integral with each other and the electric connection of the endoscope body with the imaging controlling apparatus and the illuminating light connection of the endoscope body with the light source apparatus are made separately from each other.

The sets of the cables and electric contacts relating not only to the imaging signals but also to the other signals connected with each other within the imaging controlling apparatus 50, light source apparatus 40, endoscope body and imaging signal cord as required may be made equal in the characteristic impedance.

As explained above, according to the present invention, as the light source apparatus and imaging controlling apparatus can be made separate from each other and the entrance end of the illuminating light transmitting means of the endoscope and the base end of the signal transmitting means are made integral with each other, there is an effect that the operatability of the endoscope can be improved. As the signal transmitting means relating at least to imaging signals are made substantially equal in characteristic impedance, there is an effect that the deterioration of signals can be prevented.

In this invention, it is apparent that working modes different in a wide range can be formed on the basis of this invention without deviating from the spirit and scope of the intention. This invention is not restricted by its specific working modes except as limited by the appended claims.

What is claimed is:

1. An endoscope apparatus comprising:
   an endoscope having an elongate insertable part having an observing window and illuminating window in the tip part; and image forming optical system provided at said observing window within the tip part of said insertable part and forming an object image; and illuminating light transmitting means inserted through said insertable part, opposed at the exit end to said illuminating window and emitting an illuminating light out of said illuminating window; and imaging means for imaging the object image formed by said image forming optical system; and a first signal transmitting means connected to said imaging means;
   a light source apparatus feeding the illuminating light to said illuminating light transmitting means;
   an imaging controlling apparatus controlling said imaging means;
   an integrating means integrating the entrance end of said illuminating light transmitting means and the base end of said first signal transmitting means;
   connecting parts provided at the entrance end of said illuminating light transmitting means and at the base end of said first signal transmitting means;
   a first connecting means removably connecting the entrance end of the illuminating light transmitting means in said connecting part to said light source apparatus;
   a second signal transmitting means extended from said imaging controlling apparatus and connected to said first signal transmitting means; and
   a second connecting means removably connecting the base end of the first signal transmitting means in said connecting part and the end of said second signal transmitting means with each other.

2. An endoscope apparatus according to claim 1 wherein said first signal transmitting means and second signal transmitting means relating at least to imaging signals are substantially equal in their characteristic impedances.

3. An endoscope apparatus according to claim 1 further comprising:
a third signal transmitting means connected at one end to said imaging controlling apparatus and integrated with said second signal transmitting means;
a second connecting part provided at the other end of said third signal transmitting means;
a third connecting means removably fitted to said second connecting part and provided in said integrating means;
a fourth signal transmitting means connected at one end to said third connecting means;
a third connecting part provided at the other end of said fourth signal transmitting means; and
a fourth connecting means removably fitted to said third connecting part and provided in said light source apparatus.

4. An endoscope apparatus according to claim 3 wherein said third signal transmitting means and fourth signal transmitting means are substantially equal to each other in their characteristic impedance.

5. An endoscope apparatus according to claim 1 further comprising:
a controlling means provided in said endoscope for controlling said imaging controlling apparatus;
a fifth signal transmitting means connected at one end to said controlling means and extended at the other end to said connecting part;
a sixth signal transmitting means connected at tone end to said imaging controlling apparatus, integrated with said second signal transmitting means and connected at the other end to said fifth signal transmitting means; and
a fifth connecting means removably connecting said fifth signal transmitting means and sixth signal transmitting means with each other in said connecting part.

6. An endoscope apparatus according to claim 5 wherein said fifth signal transmitting means and sixth signal transmitting means are substantially equal to each other in their characteristic impedances.

7. An endoscope apparatus according to claim 1 wherein at least one of said light source apparatus and imaging controlling apparatus is shielded.

8. An endoscope apparatus according to claim 1, 2 or 3 further comprising a holding means which can hold said second signal transmitting means at the end when not connected to said first signal transmitting means.

9. An endoscope apparatus according to claim 1, 2 or 3 wherein said imaging means is a solid state imaging device.

10. An endoscope apparatus according to claim 9 wherein said solid state imaging device is provided within the tip part of the insertable part of said endoscope.

11. An endoscope apparatus according to claim 9 wherein said endoscope is provided with an operating part at the rear end of said insertable part and an image transmitting optical system transmitting to said operating part the object image formed by said image forming optical system, and said solid state imaging device is provided in a position in which the object image transmitted by said image transmitting optical system within said operating part can be imaged.

12. An endoscope apparatus according to claim 1, 2 or 3 wherein said second signal transmitting means is formed of a curled cord.

13. An endoscope apparatus according to claim 12 wherein said imaging controlling apparatus is provided with a containing part which can contain said second signal transmitting means.

14. An endoscope apparatus according to claim 1, 2 or 3 wherein said second signal transmitting means and said imaging controlling means are removably connected with each other.

15. An endoscope apparatus according to claims 1, 2 or 3 wherein the direction of the removable connecting operation of said second connecting means is substantially perpendicular the direction of the removable fitting operation of said first connecting means.

16. An endoscope apparatus according to claim 1, 2 or 3 wherein the direction of the removable connecting operation of said second connecting means is substantially parallel with the direction of the removable fitting operation of said first connecting means.

17. An endoscope apparatus according to claim 16 further comprising a fixing means for holding the connection of said first connecting means in the case of releasing the connection by said second connecting means.

18. An endoscope apparatus according to claim 1, 2 or 3 wherein the direction of the removable connecting operation of said second connecting means is oblique to the direction of the removable connecting operation of said first connecting means.

19. An endoscope apparatus according to claim 1, 2 or 3 further comprising a sensing means for sensing whether or not said endoscope, light source apparatus and imaging controlling apparatus are connected with on another by said first connecting means and second connecting means.

20. An endoscope apparatus according to claim 19 further comprising a control mean for stopping the transmission and reception of electric signals between the light source apparatus and imaging controlling apparatus and between the endoscope and imaging controlling apparatus in case it is sensed by said sensing means that any of said endoscope, light source apparatus and imaging controlling apparatus is not connected.

21. An endoscope apparatus according to claim 19 further comprising a control means for reducing the light amount of illuminating case it is sensed by said sensing means that any of said endoscope, light source apparatus and imaging controlling apparatus is not connected.

22. An endoscope apparatus according to claim 2 wherein signal cables equal in characteristic impedance are used as said first signal transmitting means and second signal transmitting means relating at least to imaging signals.

23. An endoscope apparatus according to claim 2 wherein said second connecting means has electric contacts connecting said first signal transmitting means and second signal transmitting with each other and the characteristic impedance of said electric contacts relating at least to imaging signals is substantially equal to the characteristic impedance of said first signal transmitting means and second signal transmitting means corresponding to said electric contacts.

24. An endoscope apparatus according to claim 23 wherein electric contacts removably connect said second signal transmitting means and said imaging controlling apparatus with each other and the characteristic impedance of said electric contacts relating at least to imaging signals is substantially equal to the characteristic impedance of said second signal transmitting means corresponding to said electric contacts.

25. An endoscope apparatus according to claim 9 wherein said solid state imaging device is provided with a solid state imaging device chip including bonding pads, a substrate mounting said solid state imaging device chip, external leads supplied on said substrate, bonding wires connecting said external leads with said bonding pads, and a sealing member sealing said solid state imaging device chip and said bonding wires; and said substrate being formed by molding and only one main push-out pin trace for pulling the molding out of the mold made of a plane part supplied on the bottom surface of said substrate being provided.

26. An endoscope connected to a light source apparatus for feeding an illuminating light and an image controlling apparatus for controlling an imaging means, comprising:

an elongate insertable part having an observing window and illuminating window in the tip part;

an image forming optical system provided at said observing window within the tip part of said insertable part and forming an object image;

An illuminating light transmitting means inserted through said insertable part, opposed at the exit end to said illuminating window and emitting an illuminating light out of said illuminating window;

an imaging means for imaging the object image formed by said image forming optical system and a first signal transmitting means connected to said imaging means;

an integrating means integrating the entrance end of said illuminating light transmitting means and the base end of said first signal transmitting means with each other;

connecting parts provided at the entrance end of said illuminating light transmitting means and at the base end of said first signal transmitting means;

a first connecting means removably connecting the entrance end of the illuminating light transmitting means in said connecting part to said light source apparatus; and a second connecting means removably connecting a second signal transmitting means extended from said imaging controlling apparatus to the base end of the first signal transmitting means in said connecting part.

27. An endoscope connected to a light source apparatus feeding an illuminating light and an imaging controlling apparatus controlling an imaging means, comprising:

an elongated insertable part having an observing window and illuminating window in the tip part;

an image forming optical system provided as opposed to said observing window within the tip part of said insertable part and forming an object image;

an illuminating light transmitting means inserted through said insertable part, opposed at the exit end to said illuminating window and emitting an illuminating light out of said illuminating window;

an imaging means for imaging the object image formed by said image forming optical system and a first signal transmitting means connected to said imaging means;

an integrating means integrating the entrance end side of said illuminating light transmitting means and the base end side of said first signal transmitting means;

connecting part provided at the entrance end of said illuminating light transmitting means and at the base end of said first signal transmitting means;

a second signal transmitting means removably connected at one end to said imaging controlling apparatus and at the other end to said first signal transmitting means;

a first connecting means removable connecting the entrance end of the illuminating light transmitting means in said connecting part to said light source apparatus; and a second connecting means removably connecting said second signal transmitting means at the other end to said first signal transmitting means at the base end in said connecting part.

28. An endoscope according to claim 27 wherein said first signal transmitting means and second signal transmitting means relating at least to imaging signals are substantially equal in their characteristic impedances.

* * * * *